(12) United States Patent
Brash et al.

(10) Patent No.: US 6,649,355 B2
(45) Date of Patent: Nov. 18, 2003

(54) LIPOXYGENASE PROTEINS AND NUCLEIC ACIDS

(75) Inventors: Alan R. Brash, Nashville, TN (US); William E. Boeglin, Nashville, TN (US); Mitsuo Jisaka, Shimane (JP)

(73) Assignee: Vanderbilt University, Nashville, TN (US)

(*) Notice: Subject to any disclaimer, the term of this patent is extended or adjusted under 35 U.S.C. 154(b) by 194 days.

(21) Appl. No.: 09/764,246

(22) Filed: Jan. 17, 2001

(65) Prior Publication Data

US 2001/0046672 A1 Nov. 29, 2001

Related U.S. Application Data

(62) Division of application No. 09/061,768, filed on Apr. 16, 1998, now Pat. No. 6,204,037.

(51) Int. Cl.[7] .......................... C12N 9/04; G01N 33/48; G01N 33/53
(52) U.S. Cl. .......................... 435/7.1; 436/63; 436/189; 436/25
(58) Field of Search .......................... 435/189, 7.1, 25; 436/63

(56) References Cited

U.S. PATENT DOCUMENTS 5,571,677 A   11/1996   Gryaznov

OTHER PUBLICATIONS

Brash et al., "Discovery of a Second 15S–lipoxygenase in Humans," Proc. Natl. Acad. Sci. USA, vol. 94, p. 6148–6152, (1997).
Funk et al., "Native and Mutant 5–lipoxygenase Expression in a Baculovirus/Insect Cell System," Proc. Natl. Acad. Sci USA, vol. 86, p. 2592–2596, (1989).
Furstenberger et al., "Characterization of an 8–Lipoxygenase Activity Induced by the Phorbol Ester Tumor Promoter 12–O–Tetradecanoylphorbol–13–acetate in Mouse Skin in Vivo," J. Biol. Chem., vol. 266 (No. 24), p. 15738–15745, (1991).
Jisaka et al., "Molecular Cloning and Functional Expression of a Phorbol Ester–inducible 8S–Lipoxygenase from Mouse Skin," J. Biol. Chem., vol. 272 (No. 26), p. 24410–24416, (1997).
Krieg et al., "cDNA Cloning of a 8–Lipoxygenase and a Novel Epidermis–type Lipoxymgenase from Phorbol Ester–treated Mouse Skin," Biochim. Biophys. Acta, vol. 1391, p. 7–12, (1998).
Lee et al., "Generation of cDNA Probes Directed by Amino Acid Sequence: Cloning of Urate Oxidase," Science, vol. 239, p. 1288–1291, (1988).
Matthews et al., "Biochemistry," The Benjamin/Cummings Publ. Co., Inc. (Redwood City, CA), p. 156–161, (1990).
Nguyen et al., "Evaluation of the Role of Conserved His and Met Residues Among Lipoxygenases by Site–Directed Mutagenesis of Recombinant Human 5–Lipoxygenase," J. Biol. Chem., vol. 266 (No. 32), p. 22057–22062, (1991).
Reddy et al., "Expression, Purification, and Characterization of Porvine Leukocyte 12–Lipoxygenase Produced in teh Methylotropic Yeast, Pichia Pastoris," Biochem. Biophys. Res. Comm., vol. 205 (No. 1), p. 381–388, (Nov. 30, 1994).
Marra et al., "GenBank, Accession No. AA117154".
NCI–CGAP, "GenBank, Accession No. AA470333".

Primary Examiner—Rebecca E. Prouty
Assistant Examiner—Sheridan Swope
(74) Attorney, Agent, or Firm—Jenkins, Wilson & Taylor, P.A.

(57) ABSTRACT

Isolated and purified lipoxygenase proteins and nucleic acids are described. Particularly, a novel human 15(S) lipoxygenase (15-Lox-2) protein and cDNA and a cDNA for mouse 8S-lipoxygenase are described. Recombinant host cells, recombinant nucleic acids and recombinant proteins are also described, along with methods of producing each. Isolated and purified antibodies to 15-Lox-2 and 8-Lox, and methods of producing the same, are also described.

6 Claims, 12 Drawing Sheets

```
  1  MAEFRVRVSTGEAFGAGTWDKVSVSIVGTRGESPPLPLDNLGKEF--TAGAEEDFQVTLPEDVGRVLLLRVHKAPPVLPLLGPLAP      new 15S-LO
     | |||||     ||    ||         || | | ||      |   |||   |      || ||  ||   |||   |
  1  MGLYRIRVSTGASLYAGSNQVQLMLVGQHGEAA-----LGKRLWPARGKETELKVEVPEYLGPLLFVKLRKRHL------LKD       15S-LO 85  DAWFCRWFQL-TPPRGGHLLFPCYQWLEGAGTLVLQEGTAKVSWADHHPVLQQQRQEELQARQEMYQWKAYNPGWPHCLDEKTVED    new 15S-LO
     |||||  |   |||   ||||||  | || | | |   ||      ||   || | |   |  || |   |
 74  DAWFCNWISVQGPGAGDEVRFPCYRWVEGNGVLSLPEGTGRTVGEDPQGLFQKHREEELEERRKLYRWGNWKDGLILNMAGAKLYD    15S-LO 170  LELNIKYSTAKNANFYLQAGSAFAEMKIKGLLDRKGLWRSLNEMKRIFNFRRTPAAEHAFEHWQEDAFFASQFLNGLINPVLIRRCH   new 15S-LO
      |  |||    | |||| ||   | ||| |   |||| ||  ||||| |||        |||  | |   ||   |||  ||
160  LPVDERFLEDKRVDFEVSLAKGLADLAIKDSLNVLTCWKDLDDFNRIFWCGQSKLAERVRDSWKEDALFGYQFLNGANPVVLRRSA    15S-LO 256  YLPKNFPVTDAMVASLLGPGTSLQAELEKGSLFLVDHGILSGIQTNVINGKPQFSAAPMTLLYQSPGCGPLLPLAIQL--SQTPGP    new 15S-LO
     ||        | ||   || | |  || |   ||| | | | |||          ||       ||   | || |     |   |
246  HLPARLVFPPGM-EELQAQ---LEKELEGGTLFEADFSLLDGIKANVILCSQQHLAAPLVMLKLQPD-GKLLPMVIQLQLPRTGSP    15S-LO 340  NSPIFLPTDDKWDWLLAKTWVRNAEFSFHEALTHLLHSHLLPEVFTLATLRQLPHCHPLFKLLIPHTRYTLHINTLARELLIVPGQ    new 15S-LO
      | ||||||   |||||| || |||  |  | |    ||| |   ||| | | |||||||||| |||| || | || |||
327  PPPLFLPTDPPMAWLLAKCWVRSSDFQLHELQSHLLRGHLMAEVIVVATMRCLPSIHPIFKLIIPHLRYTLEINVRARTGLVSDMG    15S-LO 426  VVDRSTGIGIEGFSELIQRNMKQLNYSLLCLPEDIRTRGVEDIPGYYRDDGMQIWGAVERFVSEIIGIYYPSDESVQDDRELQAW     new 15S-LO
      | ||   |  ||||| |     | || | |||           | |  ||||  |   |  ||  ||||||||  ||||||
413  IFDQIMSTGGGHVQLLKQAGAFLITYSSFCPPDDLADRGILGVKSSFYAQDALRLWEIIYRYVEGIVSLHYKTDVAVKDDPELQTW    15S-LO 512  VREIFSKGFLNQESSGIPSSLETREALVQYVTMVIFTCSAKHAAVSAGQEFDSCAWMPNLPPSMQLPPPTSKGLATCEGFIATLPPV   new 15S-LO
     |||         |||           |       |||                    || ||         ||      |||
499  CREITEIGLQGAQDRGFPVSLQARDQVCHFVTMCIFTCTGQHASVHLGQLDMYSWVPNAPCTMRLPPPTTKD-ATLETVMATLPNF    15S-LO 598  NATCDVILAIWLLSKEPGDQRPLGTYPDEHFTEEAPRRSIATFQSRLAQISRGIQERNRGLIVLPYTYLDPPLIENSVSI          676   new 15S-LO
      |    |  |  |                       |   |         |                  |||
584  HQASLQMSITWQLGRRQPVMVAVGQHEEEYFSGPEPKAVLKKFREELAALDKEIEIRNAKLDMPYEYLRPSVVENSVAI           662   15S-LO new 15S-LO=15-Lox-2=(SEQ ID NO:2)
15S-LO=15-Lox-1=(SEQ ID NO:25)
```

```
  1   MAKCRVRVSTGEACGAGTWDKVSVSIVGTHGESPLVPLDHLGKEFSAGAEEDFEVTLPQDVGTVLMLRVHKAPPEVSLPLMSFRS        8-Lox
        ||  |||||||| ||||||||||||||  ||||||  ||||   |||| ||||| |||  |||||||||||||  |||   
  1   MAEFRVRVSTGEAFGAGTWDKVSVSIVGTRGESPPLPLDNLGKEFTAGAEEDFQVTLPEDVGRVLLLRVHKAPPVLPL-LGPLAP       15-Lox-2

86   DAWFCRWFELEWLPGAALHFPCYQWMLEGAGELVLREGAAKVSWQDHHPTLQDQRQKELESRQKMYSWKTYIEGWPRCLDHETVKD        8-Lox
      ||||||||  |   |||||||||||||||| |||||  ||||| |||||  ||||||  ||| |                 ||
 85   DAWFCRWFQLTPPRGGHLLFPCYQWLEGAGTLVLQEGTAKVSWADHHPVLQQQRQEELQARQEMYQWKAYNPGWPHCLDEKTVED       15-Lox-2

171   LDLNIKYSAMKQNAKLFFKAHSAYTELKVVKGLLDRTGLWRSLREMRRLFNFRKTPAAEYVFAHWQEDAFFASQFLNGINPVLIRRC      8-Lox
      | |||||| || ||  |  |  |  | |  |||| ||||| |  ||  |||| ||||| | ||||||||||||| ||| ||||||||
170   LELNIKYSTAKNANFYLQAGSAFAEMKIKGLLDRKGLWRSLNEMKRIFNFRRTPAAEHAFEHWQEDAFFASQFLNGLNPVLIRRC      15-Lox-2

256   HSLPNNFPVTDEMVAPVLGPGTSLQAELEKGSLFLVDHGILSGVHTNILNGKPQFSAAPMTLHQSSGSGPLLPIAIQLKQTPGP        8-Lox
      | ||| ||||| ||  |||||||||||||||||||||||||||  |||||||||||||||||||     ||||||  | ||||
255   HYLPKNFPVTDAMVASLLGPGTSLQAELEKGSLFLVDHGILSGIQTNVINGKPQFSAAPMTLLYQSPGGCGPLLPLAIQLSQTPGP      15-Lox-2

341   DNPIFLPSDDTWDWLLAKTWRNSEFYIHEAVTHLLHAHLIPEVFALATLRQLPRCHPLFKLLIPHIRYTLHINTLARELLVAPG        8-Lox
      |  |||| ||  ||||||||  ||  | |||||| ||||| |  ||||||||   ||||||||| |||||||||||||| |||
340   NSPIFLPTDDKWDWLLAKTWVRNAEFSFHEAALTHLLHSHLLPEVFTLATLRQLPHCHPLFKLLIPHTRYTLHINTLARELLIVPG     15-Lox-2

426   KLIDKSTGLGTGGFSDLIKRNMEQLNYSVLCLPEDIRARGVEDIPGYYYRDDGMQIWGAIKSFVSEIVSIYYPSDTSVQDDQELQ        8-Lox
             | | || | ||  || ||| || ||||||| |||||||||||||||| |     |  |||| ||||||||   |  ||
425   QVVDRSTGIGIEGFSELIQRNMKQLNYSLLCLPEDIRTRGVEDIPGYYYRDDGMQIWGAVERFVSEIIGIYYPSDESVQDDRELQ      15-Lox-2

511   AWVREIFSEGFLGRESSGMPSLLDTREALVQYITMVIFTCSAKHAAVSSGQFDSCVWMPNLPPTMQLPPPTSKGQARPESFIATL       8-Lox
      |||||||| ||| |||| | || |||| || | ||||||||||||||| ||||||| ||||||| ||||||||| | ||||||
510   AWVREIFSKGFLNQESSGIPSSLETREALVQYVTMVIFTCSAKHAAVSAGQFDSCAWMPNLPPSMQLPPPTSKGLATCEGFIATL      15-Lox-2

596   PAVNSSSYHIIALWLLSAEPGDQRPLGHYPDEHFTEDAPRRSVAAFQRKLIQISKGIRERNRGLALPYTYLDPPLIENSVSI  677   8-Lox
      | ||   |  ||||||| |||||||| |||||||| ||||| |||| |||| |  |  ||||| |||||||||||||||||
595   PPVNATCDVILALWLLSKEPGDQRPLGTYPDEHFTEEAPRRSIATFQSRLAQISRGIQERNRGLVLPYTYLDPPLIENSVSI  676   15-Lox-2
```

FIG. 6

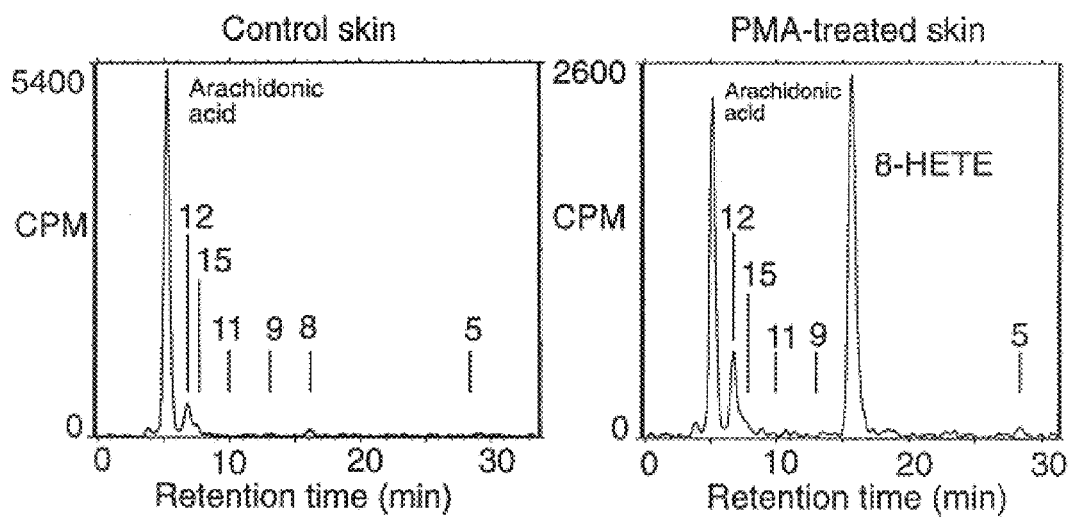
FIG. 9A
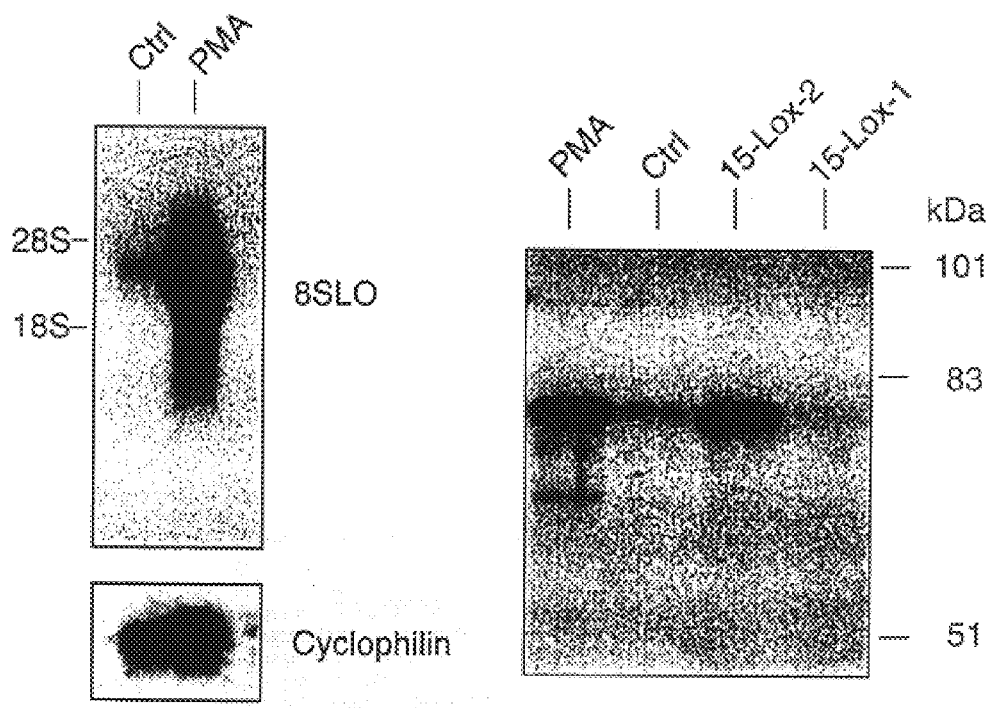
FIG. 9B
FIG. 9C

LIPOXYGENASE PROTEINS AND NUCLEIC ACIDS

CROSS REFERENCE TO RELATED APPLICATION

This application is a Divisional of U.S. patent application Ser. No. 09/061,768, filed Apr. 16, 1998, U.S. Pat. No. 6,204,037, the entire contents of which are herein incorporated by reference.

GRANT STATEMENT

This work was supported by NIH grants GM-53638 and GM-49502; and Pilot Project grants from the Vanderbilt Skin Disease Research Center (SDRC) from grant 5P30 AR41943-03 from the NIH/NIAMS and from the Center in Molecular Toxicology (USPHS ES000267). The U.S. Government has certain rights in the invention.

TECHNICAL FIELD

The present invention relates generally to isolated and purified lipoxygenase proteins and nucleic acids. More particularly, the present invention relates to an isolated and purified second type of human 15S-lipoxygenase and an isolated and purified nucleic acid encoding the same, and to an isolated and purified nucleic acid encoding a mouse 8S-lipoxygenase.

| Table of Abbreviations | |
|---|---|
| 15-Lox-1 | Reticulocyte-type of 15S-lipoxygenase |
| 15-Lox-2 | Second type of human 15S-lipoxygenase |
| 8-Lox | mouse 8S-lipoxygenase |
| PMA | Phorbol-12-myristate-13-acetate |
| H(P)ETE | Hydro(pero)xyeicosatetraenoic acid |
| HODE | Hydroxyoctadecadienoic acid |
| HPLC | High pressure liquid chromatography |
| PCR | Polymerase chain reaction |
| RACE | Rapid amplification of cDNA ends |

BACKGROUND ART

The lipoxygenases are a structurally related family of non-heme iron dioxygenases that function in the production of fatty acid hydroperoxides. Three lipoxygenases have been identified and cloned in humans. Funk, C. D. (1993) *Prog. Nuc. Acid Res. Mol. Biol.* 45:67–98; Matsumoto et al. (1988) *Proc. Natl. Acad. Sci. USA* 85: 26–30; Dixon et al. (1988) *Proc. Natl. Acad. Sci. USA* 85: 416–420; Funk et al. (1990) *Proc. Natl. Acad. Sci. USA* 87: 5638–5642; Izumi et al. (1990) *Proc. Natl. Acad. Sci. USA* 87:7477–7481; Yoshimoto et al. (1990) *Biochem. Biophys. Res. Comm.* 172:1230–1235; Sigal et al. (1988) *Biochem. Biophys. Res. Comm.* 157:457–464). They oxygenate arachidonic acid in different positions along the carbon chain and form the corresponding 5S-, 12S- or 15S-hydroperoxides (hydroperoxy-eicosatetraenoic acids, HPETEs). The three enzymes are known mainly from the blood cell types in which they are strongly expressed—the 5S-lipoxygenase of leukocytes, the 12S-lipoxygenase of platelets, and the 15S-lipoxygenase of reticulocytes, eosinophils and macrophages. While these are the most widely recognized cellular sources, selective expression is well documented in other tissues. For example, both the 12S- and 15S-lipoxygenases are detected in skin. Nugteren et al. (1987) *Biochim. Biophys. Acta* 921:135–141; Henneicke-von Zepelin et al. (1991) *J. Invest. Dermatol.* 97:291–297; Takahashi et al. (1993) *J. Biol. Chem.* 268:16443–16448; Hussain et al. (1994) *Amer. J. Physiol.* 266:C243–C253.

Potentially, the three cloned lipoxygenases could account for all enzymatic synthesis of arachidonate hydroperoxides in humans, but there are reasons to consider that other lipoxygenases may exist. For example, in the mouse there are five known lipoxygenases, three that correspond to the known human enzymes, Chen et al. (1994) *J. Biol. Chem.* 269:13979–13987; Chen et al. (1995) *J. Biol. Chem.* 270:17993–17999 and two others, Furstenberger et al. (1991) *J. Biol. Chem.* 266:15738–15745; Funk et al. (1996) *J. Biol. Chem.* 271:23338–23344.

Three of the five distinct mouse lipoxygenase enzymes are best known for their occurrence in different types of blood cells. In common with other mammals, a 5S-lipoxygenase is present in leukocytes and is responsible for synthesis of the pro-inflammatory mediators, the leukotrienes. Chen et al. (1995) *J. Biol. Chem.* 270:17993–17999; Chen et al. (1994) *Nature* 372:179–182. A 12S-lipoxygenase is found in platelets and several other tissues including skin. Nugteren et al. (1987) *Biochim. Biophys. Acta* 921:135–141; Chen et al. (1994) *J. Biol. Chem.* 269:13979–13987; Sun et al. (1996) *J. Biol. Chem.* 271:24055–24062.

A second type of 12S-lipoxygenase which is closely related in sequence to the human and rabbit "reticulocyte-type" of 15S-lipoxygenases occurs in certain macrophages. Sun et al. (1996) *J. Biol. Chem.* 271, 24055–24062. The fourth mouse lipoxygenase to be characterized is another enzyme to have 12S-lipoxygenase activity; it was cloned recently from mouse skin and has been classified as an epidermal 12S-lipoxygenase. van Dijk et al. (1995) *Biochim. Biophys. Acta* 1259:4–8; Funk et al. (1996) *J. Biol. Chem.* 271:23338–23344. All four of these murine lipoxygenases enzymes have been characterized at the cDNA and genomic levels.

The fifth known mouse lipoxygenase was described originally in 1986 by Furstenberger, Marks and colleagues as an enzyme in skin forming 8-HETE and inducible by phorbol ester treatment. Gschwendt et al. (1986) *Carcinogenesis* 7:449–455. It was shown subsequently that this enzyme forms the 8S enantiomer (Hughes et al. (1991) *Biochim. Biophys. Acta* 1081:347–354) and isolation of the corresponding hydroperoxide confirmed identification of the enzyme as a lipoxygenase. Fürstenberger et al. (1991) *J. Biol. Chem.* 266:15738–15745. Mouse skin is the only reported site of synthesis of 8S-HETE in animal tissues, and there is no indication from the literature pointing to a potential homologue of the mouse 8S-lipoxygenase in other mammals. Additionally, no nucleic acid, particularly a cDNA, which encodes this lipoxygenase has been characterized.

Despite the description in the art of the enzymes presented above, along with the catalytic activities covered by these enzymes, there remains an open question whether a lipoxygenase rather than a cytochrome P450 might account for the synthesis of 12R-hydroxy arachidonic acid (12R-HETE), Hammarström et al. (1975) *Proc. Natl. Acad. Sci. USA* 72:5130–5134; Woollard, P. M. (1986) *Biochem. Biophys. Res. Commun.* 136(1):169–175; Baer et al. (1991) *J. Lipid Research* 32:341–347; Holtzman et al. (1989) *J. Clin. Invest.* 84:1446–1453; Brash et al. (1996) *J. Biol. Chem.* 271:20549–20557, a prominent arachidonate metabolite in the skin disease of psoriasis and other proliferative dermatoses (Hammarström et al. (1975) *Proc. Natl. Acad. Sci. USA* 72:5130–5134; Baer et al. (1991) *J. Lipid Research* 32:341–347; Baer et al. (1995) *J. Invest. Dermatol.* 104:251–255).

Therefore, what is needed, then, is further characterization of lipoxygenase enzymes in vertebrates, particularly in mammals, and more particularly in humans. A novel isolated and purified lipoxygenase and a nucleic acid encoding the same would have broad utility to due its role in arachidonic acid metabolism, a critical metabolic pathway.

DISCLOSURE OF THE INVENTION

A key aspect of this invention pertains to the discovery of a novel 15S-lipoxygenase (15-Lox-2) protein and nucleic acid encoding the 15-Lox-2 protein. Preferred nucleic acid and amino acid sequences for 15-Lox-2 are described in SEQ ID NO:1 and SEQ ID NO:2.

It is another aspect of this invention that the novel 15-Lox-2 protein acts in the metabolism of arachidonic acid to 15S-Hydro(pero)xyeicosatetraenoic acid.

Another key aspect of this invention is isolation and purification of a nucleic acid encoding mouse 8S-lipoxygenase (8-Lox) A preferred embodiment of this nucleic acid is described in SEQ ID NO:3.

Thus, in one aspect, the present invention provides an isolated and purified polynucleotide that encodes a lipoxygenase polypeptide wherein the lipoxygenase polypeptide includes an iron ligand comprising a serine. Preferably, the lipoxygenase polypeptide reacts with arachidonic acid. In a preferred embodiment, a polynucleotide of the present invention is a DNA molecule from a vertebrate species. A preferred vertebrate is a mammal. A preferred mammal is a human. More preferably, a polynucleotide of the present invention encodes polypeptides designated 15-Lox-2 and 8-Lox. Even more preferred, a polynucleotide of the present invention encodes a polypeptide comprising the amino acid residue sequence of SEQ ID NO:2 or SEQ ID NO:4. Most preferably, an isolated and purified polynucleotide of the invention comprises the nucleotide base sequences of SEQ ID NO:1 or SEQ ID NO:3 or their homologues from other vertebrate species.

Yet another aspect of the present invention contemplates an isolated and purified polynucleotide comprising a base sequence that is identical or complementary to a segment of at least 10 contiguous bases of SEQ ID NO:1 wherein the polynucleotide hybridizes to a polynucleotide that encodes a lipoxygenase polypeptide wherein the lipoxygenase polypeptide includes an iron ligand comprising a serine. Preferably, the lipoxygenase polypeptide reacts with arachidonic acid. Preferably, the isolated and purified polynucleotide comprises a base sequence that is identical or complementary to a segment of at least 25 to 70 contiguous bases of SEQ ID NO:1. For example, a polynucleotide of the invention can comprise a segment of bases identical or complementary to 40 or 55 contiguous bases of the disclosed nucleotide sequences.

In another embodiment, the present invention contemplates an isolated and purified lipoxygenase polypeptide wherein the lipoxygenase polypeptide includes an iron ligand comprising a serine. Preferably, the lipoxygenase polypeptide reacts with arachidonic acid. More preferably, a polypeptide of the invention is a recombinant polypeptide. Even more preferably, a polypeptide of the present invention is 15-Lox-2. Even more preferably, a polypeptide of the present invention comprises the amino acid residue sequence of SEQ ID NO:2.

In an alternative embodiment, the present invention provides an expression vector comprising a polynucleotide that encodes a lipoxygenase polypeptide that includes an iron ligand comprising a serine. Preferably, the lipoxygenase polypeptide reacts with arachidonic acid. Also preferably, an expression vector of the present invention comprises a polynucleotide that encodes 15-Lox-2 or 8-Lox. More preferably, an expression vector of the present invention comprises a polynucleotide that encodes a polypeptide comprising the amino acid residue sequence of SEQ ID NO:2 or SEQ ID NO:4. More preferably, an expression vector of the present invention comprises a polynucleotide comprising the nucleotide base sequence of SEQ ID NO:1 or SEQ ID NO:3. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a lipoxygenase polypeptide which includes an iron ligand comprising a serine. Preferably, the lipoxygenase polypeptide reacts with arachidonic acid. SEQ ID NO:1; SEQ ID NO: 2 SEQ ID NO:3; and SEQ ID NO: 4 set forth nucleotide and amino acid sequences from the exemplary vertebrates human and mouse. Also contemplated by the present invention are homologous or biologically equivalent polynucleotides and lipoxygenase polypeptides found in other vertebrates. Preferably, a recombinant host cell of the present invention is transfected with the polynucleotide that encodes 15-Lox-2 or 8-Lox. More preferably, a recombinant host cell of the present invention is transfected with the polynucleotide sequence of SEQ ID NO:1 or SEQ ID NO:3. Even more preferably, a host cell of the invention is a eukaryotic host cell. Still more preferably, a recombinant host cell of the present invention is a vertebrate cell. Preferably, a recombinant host cell of the invention is a mammalian cell.

In another aspect, a recombinant host cell of the present invention is a prokaryotic host cell. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of a lipoxygenase polypeptide that metabolizes arachidonic acid in a manner to enable all necessary transcriptional and post-transcriptional modification.

In yet another embodiment, the present invention contemplates a process of preparing a lipoxygenase polypeptide comprising transfecting a cell with polynucleotide that encodes a lipoxygenase polypeptide which includes an iron ligand comprising a serine, to produce a transformed host cell; and maintaining the transformed host cell under biological conditions sufficient for expression of the polypeptide. Preferably, the lipoxygenase polypeptide that is produced reacts with arachidonic acid. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of the DH5α strain of *Escherichia coli*. Even more preferably, a polynucleotide transfected into the transformed cell comprises the nucleotide base sequence of SEQ ID NO:1 or SEQ ID NO:3. SEQ ID NO:1; SEQ ID NO:2; SEQ ID NO:3; and SEQ ID NO:4 set forth nucleotide and amino acid sequences for the exemplary vertebrates human and mouse. Also contemplated by the present invention are homologues or biologically equivalent lipoxygenase polynucleotides and polypeptides found in other vertebrates.

In still another embodiment, the present invention provides an antibody immunoreactive with a lipoxygenase polypeptide which includes an iron ligand comprising a serine. Preferably, the lipoxygenase polypeptide reacts with arachidonic acid. SEQ ID NO:1; SEQ ID NO:2; SEQ ID NO:3; and SEQ ID NO:4 set forth nucleotide and amino acid sequences from the exemplary vertebrates human and mouse. Also contemplated by the present invention are antibodies immunoreactive with homologues or biologically equivalent lipoxygenase polynucleotides and polypeptides found in other vertebrates. Preferably, an antibody of the invention is a monoclonal antibody. More preferably, the lipoxygenase polypeptide comprises 15-Lox-2 or 8-Lox. Even more preferably, a polypeptide comprises the amino acid residue sequence of SEQ ID NO:2 or SEQ ID NO:4.

In another aspect, the present invention contemplates a process of producing an antibody immunoreactive with a lipoxygenase polypeptide which includes an iron ligand comprising a serine, the process comprising the steps of (a) transfecting a recombinant host cell with a polynucleotide that encodes a lipoxygenase polypeptide which includes an iron ligand comprising a serine; (b) culturing the host cell under conditions sufficient for expression of the polypeptide; (c) recovering the polypeptide; and (d) preparing the antibody to the polypeptide. Preferably, the lipoxygenase polypeptide reacts with arachidonic acid. SEQ ID NO:1; SEQ ID NO:2; SEQ ID NO:3; and SEQ ID NO:4 set forth nucleotide and amino acid sequences from the exemplary vertebrates mouse and human. Preferably, the host cell is transfected with the polynucleotide of SEQ ID NO:1 or SEQ ID NO:3. Even more preferably, the present invention provides an antibody prepared according to the process described above. Also contemplated by the present invention is the use of homologues or biologically equivalent polynucleotides and polypeptides found in other vertebrates to produce antibodies.

Alternatively, the present invention provides a process of detecting a lipoxygenase polypeptide that metabolizes arachidonic acid, wherein the process comprises immunoreacting the polypeptide with an antibody prepared according to the process described above to form an antibody-polypeptide conjugate, and detecting the conjugate.

In yet another embodiment, the present invention contemplates a process of detecting a messenger RNA transcript that encodes a lipoxygenase polypeptide which includes an iron ligand comprising a serine, wherein the process comprises hybridizing the messenger RNA transcript with a polynucleotide sequence that encodes that polypeptide to form a duplex; and detecting the duplex. Alternatively, the present invention provides a process of detecting a DNA molecule that encodes a lipoxygenase polypeptide, wherein the process comprises hybridizing DNA molecules with a polynucleotide that encodes a lipoxygenase polypeptide which includes an iron ligand comprising a serine to form a duplex; and detecting the duplex. For both such processes, it is preferred that the detected lipoxygenase polypeptide is capable of reacting with arachidonic acid.

In another aspect, the present invention contemplates a diagnostic assay kit for detecting the presence of a lipoxygenase polypeptide in a biological sample, where the kit comprises a first container containing a first antibody capable of immunoreacting with a lipoxygenase polypeptide which includes an iron ligand comprising a serine, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of a lipoxygenase polypeptide, the kits comprising a first container that contains a second polynucleotide identical or complementary to a segment of at least 10 contiguous nucleotide bases of a polynucleotide that encodes a lipoxygenase polypeptide which includes an iron ligand comprising a serine. Preferably, the polynucleotide encodes a lipoxygenase polypeptide capable of reacting with arachidonic acid. More preferably, the polynucleotide encodes 15-Lox-2 or 8-Lox.

In another embodiment, the present invention contemplates a diagnostic assay kit for detecting the presence, in a biological sample, of an antibody immunoreactive with a lipoxygenase polypeptide, the kit comprising a first container containing a lipoxygenase polypeptide which includes an iron ligand comprising a serine that immunoreacts with the antibody, with the polypeptide present in an amount sufficient to perform at least one assay. Preferably, the lipoxygenase polypeptide is capable of reacting with arachidonic acid. More preferably, the polypeptide comprises 15-Lox-2 or 8-Lox.

The foregoing aspects and embodiments have broad utility given the biological significance of the arachidonic acid pathway, as is known in the art. By way of example, the foregoing aspects and embodiments are useful in the preparation of screening assays and assay kits that are used to identify compounds that affect arachidonic acid metabolism, or that are used to detect the presence of the proteins and nucleic acids of this invention in biological samples. Additionally, it is well known that isolated and purified polypeptides have utility as feed additives for livestock and further polynucleotides encoding the polypeptides are thus useful in producing the polypeptides.

Following long-standing patent law convention, the terms "a" and "an" mean "one or more" when used in this application, including the claims.

Some of the aspects and objects of the invention having been stated hereinabove, other aspects and objects will become evident as the description proceeds, when taken in connection with the accompanying drawings as best described hereinbelow.

BRIEF DESCRIPTION OF THE DRAWINGS

FIG. 1 shows sequence alignment of human 15S-lipoxygenases. The top line shows the amino acid sequence (SEQ ID NO:2) deduced from the new human lipoxygenase (15-Lox-2) cDNA, in alignment with the sequence of the previously reported human 15S-lipoxygenase (15-Lox-1) (SEQ ID NO:25). Sigal et al. (1988) Biochem. Biophys. Res. Comm. 157: 457–464. The consensus sequences used in PCR cloning are underlined, and five putative iron ligands (H373, H378, H553, S557, I676-15-Lox-2; H360, H365, H540, H544, I662-15-Lox-1) are in bold. Two clones of the new cDNA were sequenced: there was a single nucleotide difference (position 1263 in the open reading frame, C or T) which did not change the deduced amino acid sequence. The new cDNA sequence (SEQ ID NO:1) is available in the GenBank™/EMBL Data Bank with accession number U78294.

FIG. 2A shows reversed-phase HPLC analysis of the products using a Beckman 5µ ODS Ultrasphere column (25×0.46 cm) with a Bio-Rad 5S ODS guard column, a solvent system of methanol:water:glacial acetic acid (80:20:0.01, by volume), and a flow rate of 1.1 ml/min with on-line detection of radiolabeled products using a Packard Flo-One Radiomatic detector. Retention times of HETE standards are indicated on chromatogram. The small peak on the front shoulder of the 15-HETE is 15-keto-eicosatetraenoic acid.

FIG. 2B shows chiral analysis of the methyl ester derivative of the 15-HETE product using a Chiralcel OB column with a solvent of hexane:isopropanol (100:2, v/v) and a flow rate of 1.1 ml/min.

FIG. 4A depicts RT-PCR wherein RNA samples were treated with DNAse 1, then reverse transcribed to cDNA. PCR reactions were run using two primer sets (1 and 2, see Experimental Procedures of Example 1) with human cornea cDNA as template, and also with rabbit cornea cDNA and buffer (H$_2$O) alone as negative controls. Bands of the correct sizes, 589 bp and 351 bp, are detected in human cornea; the larger band was subcloned and sequenced, confirming the identity to the lipoxygenase cDNA cloned from skin.

FIG. 4B depicts a Northern analysis of human eye tissues. The band in cornea mRNA at about 2.5–3 KB corresponds to the new lipoxygenase transcript.

FIGS. 5A–C show nucleotide (SEQ ID NO:3) and deduced amino acid (SEQ ID NO:4) sequences of the mouse 8S lipoxygenase. The sequence is from two identical cDNA library clones, except for the 5' UTR, which was obtained by 5' RACE. The consensus sequences used in PCR cloning are underlined. Seven PCR clones encoding the open reading frame and which expressed 8S-lipoxygenase activity were also fully sequenced. These contained multiple nucleotide substitutions which changed the encoded amino acid sequence yet had no apparent detrimental effect on their expressed 8S-lipoxygenase activity: clone #G2, 112A (Leu to Met), 227-C (Val to Ala), 1607-A (Arg to Gln) clone #G5, 227-C (Val to Ala), 1607-A (Arg to Gln); clone #G11, 227-C (Val to Ala), 1607-A (Arg to Gln); clone #K1, 227-C (Val to Ala); clone #K2, same amino acid sequence as library clone; clone #K7, 1237-G (Ile to Val); clone #K12, 95-G (Glu to Gly), 173-G (Pro to Arg). The cDNA sequence is available in GenBank with accession no. U93277.

FIG. 6 shows alignment of mouse 8S-lipoxygenase with the second type of human 15S-lipoxygenase (15-Lox-2). The top line shows the amino acid sequence (SEQ ID NO:4) deduced from the mouse 8S-lipoxygenase cDNA, in alignment with the amino acid sequence (SEQ ID NO:2) of the second type of human 15S-lipoxygenase. Five putative iron ligands are in boldface (H374, H379, H554, S558, I677-8-Lox; H373, H378, H553, S557, I676-15-Lox-2).

FIG. 7A: The products were analyzed by normal phase HPLC using an Alltech 5µ silica column (25×0.46 cm) and a solvent of hexane/isopropanol/glacial acetic acid (100:2:0.1, by volume) at a flow rate of 1.1 ml/min. The column effluent was monitored using a Hewlett-Packard 1040A diode array detector with an on-line Packard Flo-one radioactive detector.

FIG. 7B: The chirality of the 8-HETE product was analyzed as the methyl ester derivative using a Chiralcel OD column (25×0.46 cm) and a solvent of hexane/isopropanol (100:2, by volume) at a flow rate of 1.1 ml/min.

FIG. 7C shows Western analyses of 8S-lipoxygenase expressed in Hela cells, HEK cells and the enzyme from mouse skin. Lane 1: 15-Lox-1 expressed in HEK cells (antibody does not recognize this protein). Lane 2: 15-Lox-2, HEK cells. Lane 3: 8S-lipoxygenase in HEK cells. Lane 4: PMA-treated mouse skin. Lane 5: 8S-lipoxygenase in Hela cells. Lane 6: 15-Lox-2 in Hela cells. All lanes were loaded with 5 µg protein, except lane 4 had only 2.5 µg protein.

FIG. 8A: Normal phase-HPLC of the products, analyzed after reduction with triphenylphosphine.

FIG. 8B: Chiral HPLC analysis of the 9-HODE methyl ester.

FIGS. 9A–C shows the effect of phorbol ester on 8S-lipoxygenase expression in mouse skin.

FIG. 9A: Normal-phase HPLC analysis of 8S-lipoxygenase activity in homogenates of back skin of 7–8-day-old black Swiss pups following 24 hr treatment with vehicle (acetone) or phorbol ester (50 nmol).

FIG. 9B: Northern analysis.

FIG. 9C: Western analysis.

DETAILED DESCRIPTION OF THE INVENTION

Figures 2A, 2B:
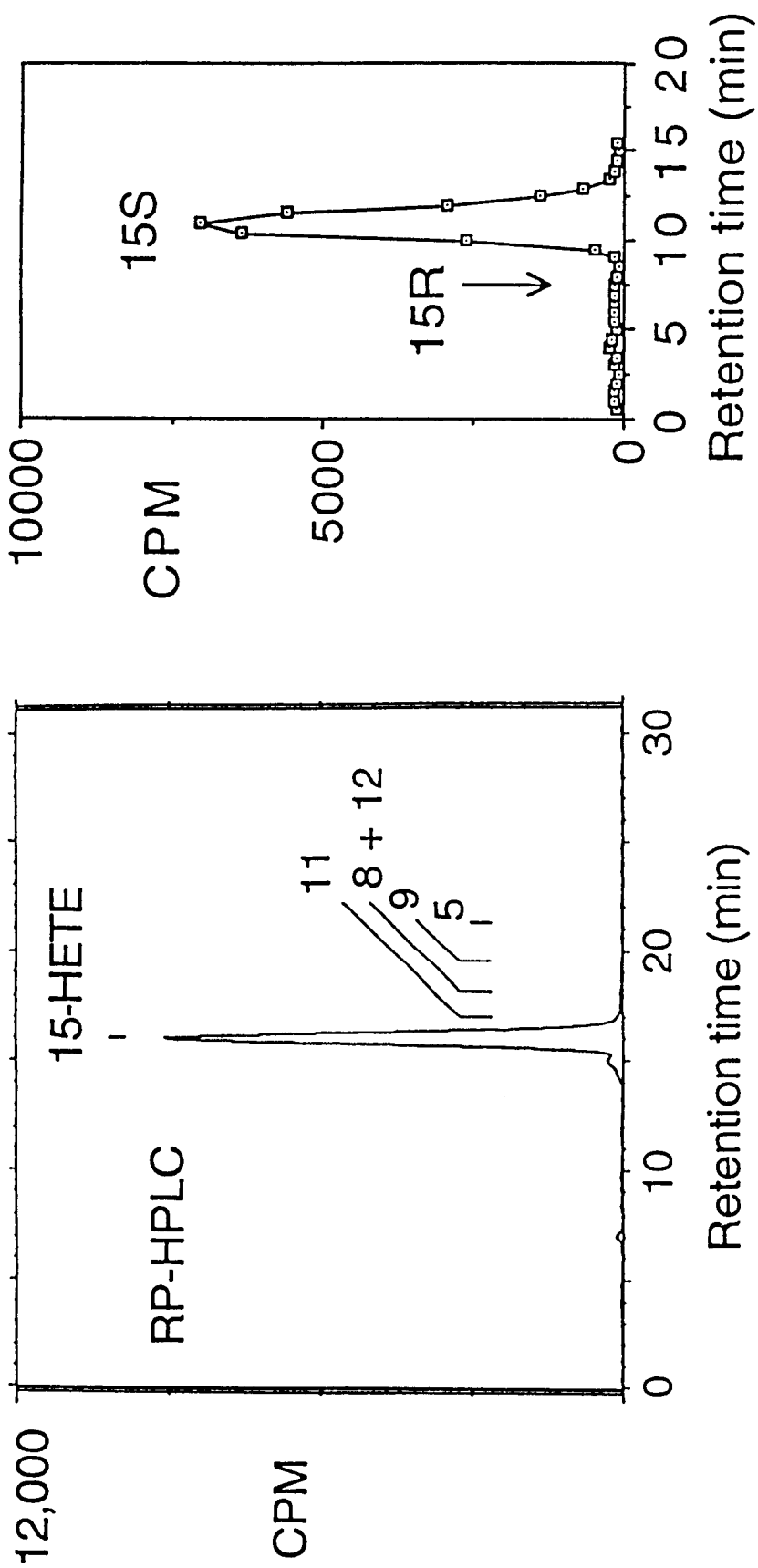
FIGS. 2A–B show expression in HEK 293 cells: identification of the 15S-HETE product. Following transient expression of the cDNA, the HEK 293 cells were sonicated in 50 mM Tris (pH 7.5) containing 100 mM NaCl, then incubated with [$^{14}$C]arachidonic acid (50 µM) for 30 min at 37° C., and the products extracted as described IN Brash et al. (1996) *J. Biol. Chem.* 271:20549–20557.

The lipoxygenase metabolism of arachidonic acid occurs in specific blood cell types and epithelial tissues, and is activated in inflammation and tissue injury. In the course of studying lipoxygenase expression in human skin, a previously unrecognized enzyme was detected and characterized that at least partly accounts for the 15S-lipoxygenase metabolism of arachidonic acid in certain epithelial tissues. The cDNA was cloned from human hair roots, and expression of the mRNA was detected also in prostate, lung, and cornea; an additional sixteen human tissues, including peripheral blood leukocytes, were negative for the mRNA. The cDNA encodes a protein of 676 amino acids with a calculated molecular weight of about 76 kD. The amino acid sequence has approximately 40% identity to the known human 5S-, 12S- and 15S-lipoxygenases.

When expressed in human embryonic kidney (HEK) 293 cells, the new enzyme converts arachidonic acid exclusively to 15S-hydroperoxyeicosatetraenoic acid, while linoleic acid is less well metabolized. These features contrast with the previously reported 15S-lipoxygenase which oxygenates arachidonic acid mainly at C-15, but also partly at C-12, and for which linoleic acid is an excellent substrate. The different catalytic activities and tissue distribution suggest a distinct function for the new enzyme compared to the previously reported human 15S-lipoxygenase.

It is known that human hair roots metabolize arachidonic acid (Henneicke-von Zepelin et al. (1991) *J. Invest. Dermatol.* 97:291–297), and that in addition to a relatively prominent synthesis of 12S-HETE and 15S-HETE, formation of minor amounts of 12R-HETE is detectable. (Baer et al. (1993) *J. Lipid Research* 34:1505–1514). Therefore freshly plucked human hair follicles were as a source of RNA for the RT-PCR experiments described in Example 1. As described in Example 1, these experiments led to the detection of a new lipoxygenase, a 15S-lipoxygenase (referred to herein as "15-Lox-2") with a distinctive distribution in tissues.

Definitions and Techniques Affecting Gene Products and Genes

The present invention concerns DNA segments, isolatable from vertebrate tissue, and preferably mammalian tissue, which are free from genomic DNA and which are capable of conferring arachidonic acid metabolism activity in a recombinant host cell when incorporated into the recombinant host cell. As used herein, the term "mammalian tissue" refers to, among others, normal mammalian epithelial tissues, as exemplified by, but not limited to, human embryonic kidney (HEK) 293 cell lines. DNA segments capable of conferring arachidonic acid metabolism activity may encode complete lipoxygenase gene products, cleavage products and biologically actively functional domains thereof.

The terms "lipoxygenase gene product", "lipoxygenase", "Lox", "15-Lox-2 gene product", "15-Lox-2", "8-Lox gene product" and "8-Lox" as used in the specification and in the claims refer to proteins having amino acid sequences which are substantially identical to the respective native lipoxygenase amino acid sequences and which are biologically active in that they are capable of reacting with arachidonic acid or are capable of cross-reacting with an anti-Lox antibody raised against a lipoxygenase, such as 15-Lox-2 or 8-Lox. Such sequences are disclosed herein. The terms "lipoxygenase gene product", "lipoxygenase", "Lox", "15-Lox-2 gene product", "15-Lox-2","8-Lox gene product" and "8-Lox" also include analogs of lipoxygenase molecules which exhibit at least some biological activity in common with native lipoxygenase, 15-Lox-2, or 8-Lox. Furthermore, those skilled in the art of mutagenesis will appreciate that other analogs, as yet undisclosed or undiscovered, may be used to construct lipoxygenase analogs. There is no need for a "lipoxygenase" or "Lox", or a "15-Lox-2" or "8-Lox" to comprise all, or substantially all, of the amino acid sequence of the native lipoxygenase genes. Shorter or longer sequences are anticipated to be of use in the invention.

The terms "lipoxygenase gene", "15-lox-2 gene" and "8-Lox gene" refer to any DNA sequence that is substantially identical to a DNA sequence encoding a lipoxygenase, 15-Lox-2 or 8-Lox as defined above. The terms also refer to RNA, or antisense sequences, compatible with such DNA sequences. A "lipoxygenase gene", a "15-lox-2 gene" or a "8-Lox gene" may also comprise any combination of associated control sequences.

The term "substantially identical", when used to define either a lipoxygenase, a 15-lox-2 or a 8-Lox amino acid sequence, or a lipoxygenase, a 15-lox-2 or a 8-Lox nucleic acid sequence, means that a particular sequence, for example, a mutant sequence, varies from the sequence of a natural lipoxygenase, 15-lox-2 or 8-Lox by one or more deletions, substitutions, or additions, the net effect of which is to retain at least some of biological activity of the lipoxygenase, the 15-lox-2 or the 8-Lox protein. Alternatively, DNA analog sequences are "substantially identical" to specific DNA sequences disclosed herein if: (a) the DNA analog sequence is derived from coding regions of the natural lipoxygenase, 15-lox-2 or 8-Lox gene; or (b) the DNA analog sequence is capable of hybridization of DNA sequences of (a) under moderately stringent conditions and which encode biologically active lipoxygenase, 15-lox-2 or 8-Lox gene; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

Percent Similarity

Percent similarity may be determined, for example, by comparing sequence information using the GAP computer program, available from the University of Wisconsin Geneticist Computer Group. The GAP program utilizes the alignment method of Needleman et al. 1970, as revised by Smith et al. 1981. Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

Nucleic Acid Sequences

In certain embodiments, the invention concerns the use of lipoxygenase genes and gene products, such as the 15-lox-2 and 8-Lox gene products, that include within their respective sequences a sequence which is essentially that of a lipoxygenase, 15-lox-2 or 8-Lox gene, or the corresponding proteins. The term "a sequence essentially as that of lipoxygenase, 15-lox-2 or 8-Lox gene or gene product", means that the sequence substantially corresponds to a portion of a lipoxygenase, 15-lox-2 or 8-Lox gene or gene product and has relatively few bases or amino acids (whether DNA or protein) which are not identical to those of a lipoxygenase, 15-lox-2 or 8-Lox gene or gene product, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a lipoxygenase, 15-lox-2 or 8-Lox gene or gene product, will be sequences which are "essentially the same".

Lipoxygenase, 15-lox-2 and 8-Lox genes which have functionally equivalent codons are also covered by the invention. The term "functionally equivalent codon" is used herein to refer to codons that encode the same amino acid, such as the six codons for arginine or serine, and also to refer to codons that encode biologically equivalent amino acids (see Table 1).

TABLE 1

Functionally Equivalent Codons.

| Amino Acids | | | Condons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See, e.g., Wetmur & Davidson, 1968).

Probe sequences may also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a lipoxygenase, 15-lox-2 or 8-Lox gene product refers to a DNA segment which contains lipoxygenase, 15-lox-2 or 8-Lox coding sequences, yet is isolated away from, or purified free from, total genomic DNA of Homo sapiens. Included within the term "DNA segment" are DNA segments and smaller fragments of such segments, and also recombinant vectors, including, for example, plasmids, cosmids, phages, viruses, and the like.

Similarly, a DNA segment comprising an isolated or purified lipoxygenase, 15-lox-2 or 8-Lox gene refers to a DNA segment including lipoxygenase, 15-lox-2 or 8-Lox coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the lipoxygenase, 15-lox-2 or 8-Lox gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a 15-Lox-2 protein that includes within its amino acid sequence the amino acid sequence of SEQ ID NO:2. In other particular embodiments, the invention concerns isolated DNA segments and recombinant vectors incorporating DNA sequences which encode a protein that includes within its amino acid sequence the amino acid sequence of the 15-Lox-2 protein corresponding to human epithelial tissue.

In particular embodiments, the invention concerns isolated DNA segments and recombinant vectors incorporating DNA sequences which encode a 8-Lox protein that includes within its amino acid sequence the amino acid sequence of SEQ ID NO:4. In other particular embodiments, the invention concerns isolated DNA segments and recombinant vectors incorporating DNA sequences which encode a protein that includes within its amino acid sequence the amino acid sequence of the 8-Lox protein corresponding to mouse epithelial tissue.

It will also be understood that this invention is not limited to the particular nucleic acid and amino acid sequences of SEQ ID NOS:1, 2, 3 and 4. Recombinant vectors and isolated DNA segments may therefore variously include the 15-Lox-2 and 8-Lox encoding regions themselves, include coding regions bearing selected alterations or modifications in the basic coding region, or include encoded larger polypeptides which nevertheless include 15-Lox-2 or 8-Lox encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in SEQ ID NO:2 or SEQ ID NO:4. Naturally, where the DNA segment or vector encodes a full length 15-Lox-2 or 8-Lox gene product, the most preferred sequences are those which are essentially as set forth in SEQ ID NO:1 and SEQ ID NO:3 and which encode a protein that exhibits arachidonic acid reactivity in HEK 293 cells, as may be determined by HPLC analysis, as disclosed herein.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of SEQ ID NO:2, will be sequences which are "essentially as set forth in SEQ ID NO:2". The term "a sequence essentially set forth in SEQ ID NO:4" has a similar meaning.

In particular embodiments, the invention concerns gene therapy methods that use isolated DNA segments and recombinant vectors incorporating DNA sequences which encode a protein that includes within its amino acid sequence an amino acid sequence in accordance with SEQ ID NO:2 or in accordance with SEQ ID NO:4, SEQ ID NO:2 and SEQ ID NO:4 derived from epithelial tissue from Homo sapiens. In other particular embodiments, the invention concerns isolated DNA sequences and recombinant DNA vectors incorporating DNA sequences which encode a protein that includes within its amino acid sequence the amino acid sequence of the 15-Lox-2 protein from human epithelial tissue, or which encode a protein that includes within its amino acid sequence the amino acid sequence of the 8-Lox protein from mouse epithelial tissue.

In certain other embodiments, the invention concerns isolated DNA segments and recombinant vectors that include within their sequence a nucleic acid sequence essentially as set forth in SEQ ID NO:1, or a nucleic acid sequence essentially as set forth in SEQ ID NO:3. The term "essentially as set forth in SEQ ID NO:1" is used in the same sense as described above and means that the nucleic acid sequence substantially corresponds to a portion of SEQ ID NO:1, respectively, and has relatively few codons which are not identical, or functionally equivalent, to the codons of SEQ ID NO:1, respectively. Again, DNA segments which encode gene products exhibiting arachidonic acid metabolism activity of the 15-Lox-2 and 8-Lox gene products will be most preferred. The term "functionally equivalent codon" is used herein to refer to codons that encode the same amino acid, such as the six codons for arginine or serine, and also to refer to codons that encode biologically equivalent amino acids (see Table 1). The term "essentially as set forth in SEQ ID NO:3" has a similar meaning.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1 or SEQ ID NO:3, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent 15-Lox-2 and 8-Lox proteins and peptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test 15-Lox-2 and 8-Lox mutants in order to examine arachidonic acid reactivity at the molecular level.

If desired, one may also prepare fusion proteins and peptides, e.g., where the 15-Lox-2 or 8-Lox coding regions are aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the 15-Lox-2 or 8-Lox gene(s), e.g., in epithelial cells, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a 15-Lox-2 or 8-Lox gene in its natural environment. Such promoters may include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, specifically incorporated herein by reference. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccina virus promoter, which is more fully described below.

As mentioned above, in connection with expression embodiments to prepare recombinant 15-Lox-2 and 8-Lox proteins and peptides, it is contemplated that longer DNA segments will most often be used, with DNA segments encoding the entire 15-Lox-2 or 8-Lox protein, functional domains or cleavage products thereof, being most preferred. However, it will be appreciated that the use of shorter DNA segments to direct the expression of 15-Lox-2 and 8-Lox peptides or epitopic core regions, such as may be used to generate anti-15-Lox-2 or anti-8-Lox antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length on the order of about 5,600 nucleotides for a protein in accordance with SEQ ID NO:2 or a minimum coding length on the order of about 10,300 nucleotides for a protein in accordance with SEQ ID NO:4.

Naturally, the present invention also encompasses DNA segments which are complementary, or essentially complementary, to the sequence set forth in SEQ ID NO:1 or the sequence set forth in SEQ ID NO:3. The terms "complementary" and "essentially complementary" are defined above. Excepting intronic or flanking regions, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides of SEQ ID NO:1 or to the nucleotides of SEQ ID NO:3, will be respectively sequences which are "essentially as set forth in SEQ ID NO:1" and will be sequences which are "essentially as set forth in SEQ ID NO:3". Sequences which are essentially the same as those set forth in SEQ ID NO:1 or as those set forth in SEQ ID NO:3 may also be functionally defined as sequences which are capable of hybridizing to a nucleic acid segment containing the complement of SEQ ID NO:1 or to a nucleic acid segment containing the complement of SEQ ID NO:3 under relatively stringent conditions. Suitable relatively stringent hybridization conditions are described herein and will be well known to those of skill in the art.

Biologically Functional Equivalents

As mentioned above, modification and changes may be made in the structure of the lipoxygenase proteins and peptides, including 15-Lox-2 and 8-Lox, described herein and still obtain a molecule having like or otherwise desirable characteristics. For example, certain amino acids may be substituted for other amino acids in a protein structure without appreciable loss of interactive binding capacity with structures such as, for example, C-15 carbon or C-8 carbon of arachidonic acid. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the lipoxygenase proteins and peptides, including 15-Lox-2 and 8-Lox, (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where it any changes, for example, in an iron ligand moiety of 15-Lox-2 that render the peptide incapable of metabolism of arachidonic acid to 15S-Hydro(pero)xyeicosatetraenoic acid would result in a loss of utility of the resulting peptide for the present invention.

Amino acid substitutions, such as those which might be employed in modifying the lipoxygenase proteins and peptides, including 15-Lox-2 and 8-Lox, described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); praline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within +2 is preferred, those which are within +1 are particularly preferred, and those within +0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4)

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Sequence Modification Techniques

Modifications to the lipoxygenase proteins and peptides, including 15-Lox-2 and 8-Lox, described herein may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (e.g., Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes, for example, the 15-Lox-2 and the 8-Lox gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful 15-Lox-2, 8-Lox or other arachidonic acid metabolizing species and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

Other Structural Equivalents

In addition to the lipoxygenase peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the lipoxygenase gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., the 15-Lox-2 promoter for 15-Lox-2) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, the 15-Lox-2 or 8-Lox genes, it is proposed that one will desire to preferably employ a vector construct that will deliver the desired gene to the affected cells. This will, of course, generally require that the construct be delivered to the targeted cells, for example, epthelial cells. It is proposed that this may be achieved most preferably by introduction of the desired gene through the use of a viral vector to carry either the 15-Lox-2 sequence or the 8-Lox sequence to efficiently infect the cells. These vectors will preferably be an adenoviral, a retroviral, a vaccinia viral vector or adeno-associated virus. These vectors are preferred because they have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Where the 15-Lox-2 or 8-Lox genes themselves are employed it will be most convenient to simply use the wild type 15-Lox-2 gene or 8-Lox gene directly. However, it is contemplated that certain regions of either the 15-Lox-2 gene or the 8-Lox gene may be employed exclusively without employing the entire wild type 15-Lox-2 or 8-Lox gene. It is proposed that it will ultimately be preferable to employ the smallest region needed to regulate the metabolism of arachidonic acid to 15S-hydro(pero) xyeicosatetraenoic acid or to 8S-hydro(pero) xyeicosatetraenoic acid so that one is not introducing unnecessary DNA into cells which receive either a 15-Lox-2 gene construct or an 8-Lox gene construct. Techniques well known to those of skill in the art, such as the use of restriction enzymes, will allow for the generation of small regions of the 15-Lox-2 or 8-Lox genes. The ability of these regions to regulate the metabolism of arachidonic acid to 15S-hydro(pero)xyeicosatetraenoic acid or to 8S-hydro (pero)xyeicosatetraenoic acid can easily be determined by the assays reported in the Examples. In general, techniques for assessing metabolism of arachidonic acid to 15S-Hydro (pero)xyeicosatetraenoic acid or to 8S-hydro(pero) xyeicosatetraenoic acid are well known in the art.

Generation of Antibodies

In still another embodiment, the present invention provides an antibody immunoreactive with a polypeptide of the present invention. Preferably, an antibody of the invention is a monoclonal antibody. Means for preparing and characterizing antibodies are well known in the art (See, e.g., *Antibodies A Laboratory Manual*, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with a lipoxygenase polypeptide, such as 15-Lox-2 or 8-Lox, the process comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the lipoxygenase polypeptide is capable of metabolizing arachidonic acid. Even more preferably, the present invention provides antibodies prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 mg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5\times10^7$ to $2\times10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma ceils are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

Detecting a Polynucleotide or a Polypeptide of the Present Invention

Alternatively, the present invention provides a process of detecting a polypeptide of the present invention, wherein the process comprises immunoreacting the polypeptides with antibodies prepared according to the process described above to form antibody-polypeptide conjugates, and detecting the conjugates.

In yet another embodiment, the present invention contemplates a process of detecting messenger RNA transcripts that encode a polypeptide of the present invention, wherein the process comprises hybridizing the messenger RNA transcripts with polynucleotide sequences that encode the polypeptide to form duplexes; and detecting the duplex. Alternatively, the present invention provides a process of detecting DNA molecules that encode a polypeptide of the present invention, wherein the process comprises hybridizing DNA molecules with a polynucleotide that encodes that polypeptide to form duplexes; and detecting the duplexes.

Screening Assays

In yet another aspect, the present invention contemplates a process of screening substances for their ability to affect arachidonic acid metabolism comprising the steps of providing a cell that contains a functional polypeptide of the present invention and testing the ability of selected substances to affect arachidonic acid metabolism in that cell.

Utilizing the methods and compositions of the present invention, screening assays for the testing of candidate substances can be derived. A candidate substance is a substance which potentially can promote or inhibit arachidonic acid metabolism, by binding or other intramolecular interaction, with a lipoxygenase polypeptide, such as 15-Lox-2 or 8-Lox, that metabolizes arachidonic acid.

A screening assay of the present invention generally involves determining the ability of a candidate substance to affect metabolism of arachidonic acid in a target cell, such as the screening of candidate substances to identify those that inhibit or promote metabolism of arachidonic acid. Target cells can be either naturally occurring cells known to contain a polypeptide of the present invention or transformed cell produced in accordance with a process of transformation set forth hereinbefore.

As is well known in the art, a screening assay provides a cell under conditions suitable for testing arachidonic acid metabolism. These conditions include but are not limited to pH, temperature, tonicity, the presence of relevant factors involved in arachidonic acid metabolism (e.g., metal ions such as for example $Ca^{++}$, growth factor, interleukins, or colony stimulating factors), and relevant modifications to the polypeptide such as glycosylation or prenylation. It is contemplated that a polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of arachidonic acid metabolism in specific cells. Such factors include, for example, the presence and absence (withdrawal) of growth factor, interleukins, or colony stimulating factors.

In one embodiment, a screening assay is designed to be capable of discriminating candidate substances having selective ability to interact with one or more of the polypeptides of the present invention but which polypeptides are without a substantially overlapping activity with another of those polypeptides identified herein.

Screening Assays for a Polypeptide of the Present Invention

The present invention provides a process of screening a biological sample for the presence of a lipoxygenase polypeptide, such as 15-Lox-2 or 8-Lox. Preferably, the lipoxygenase polypeptide reacts with arachidonic acid. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$M, exposure time is from about 10 minutes to about 200 minutes.

The presence of polypeptide in the sample is detected by detecting the formation and presence of antibody-polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art. Commercial kits are available.

Screening Assay for Anti-Polypeptide Antibody

In another aspect, the present invention provides a process of screening a biological sample for the presence of antibodies immunoreactive with a lipoxygenase polypeptide, such as 15-Lox-2 or 8-Lox. Preferably the lipoxygenase polypeptide reacts with arachidonic acid. In accordance with such a process, a biological sample is exposed to a lipoxygenase polypeptide, such as 15-Lox-2 or 8-Lox, under biological conditions and for a period of time sufficient for antibody-polypeptide conjugate formation and the formed conjugates are detected.

Screening Assay for Polynucleotide That Encodes a Lipoxygenase Polypeptide, Such as 15-Lox-2 or 8-Lox A DNA molecule and, particularly a probe molecule, can be used for hybridizing as an oligonucleotide probe to a DNA source suspected of encoding a lipoxygenase polypeptide, such as 15-Lox-2 or 8-Lox. Preferably the lipoxygenase polypeptide reacts with arachidonic acid. The probing is usually accomplished by hybridizing the oligonucleotide to a DNA source suspected of possessing a lipoxygenase gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the polypeptide family and related polypeptides from a DNA library potentially containing such sequences; (3) primers for hybridizing to related sequences for the purpose of amplifying those sequences; (4) primers for altering native lipoxygenase DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected lipoxygenase gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as that shown in SEQ ID NO:1. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M-0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+ C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Assay Kits

In another aspect, the present invention contemplates diagnostic assay kits for detecting the presence of a polypeptide of the present invention in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a diagnostic kit for screening agents. Such a kit can contain a polypeptide of the present invention. The kit can contain reagents for detecting an interaction between an agent and a receptor of the present invention. The provided reagent can be radiolabelled. The kit can contain a known radiolabelled agent capable of binding or interacting with a receptor of the present invention.

In an alternative aspect, the present invention provides diagnostic assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, SEQ ID NO:1 or SEQ ID NO:3.

In another embodiment, the present invention contemplates diagnostic assay kits for detecting the presence, in a biological sample, of antibodies immunoreactive with a polypeptide of the present invention, the kits comprising a first container containing a lipoxygenase polypeptide, such as 15-Lox-2 or 8-Lox, that immunoreacts with the antibodies, with the polypeptide present in an amount sufficient to perform at least one assay. Preferably, the lipoxygenase polypeptide metabolizes arachidonic acid. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

The following examples have been included to illustrate preferred modes of the invention. Certain aspects of the following examples are described in terms of techniques and procedures found or contemplated by the present inventors to work well in the practice of the invention. These examples are exemplified through the use of standard laboratory practices of the inventors. In light of the present disclosure and the general level of skill in the art, those of skill will appreciate that the following examples are intended to be exemplary only and that numerous changes, modifications and alterations can be employed without departing from the spirit and scope of the invention.

EXAMPLE 1

Isolation of a Second 15S-Lipoxygenase (15-lox-2)

Preparation of Total RNA, and cDNA Synthesis

For each RNA preparation, about 50 human scalp hairs were plucked individually from a volunteer. About 30 hair roots, mainly from anagen follicles (Baden et al. (1979) *J. Amer. Acad. Dermatol.* 1:121–122), were cut off and dropped into 1 ml of guanidinium thiocyanate solution, the lysis buffer from the RNeasy RNA extraction kit (Qiagen). After a brief sonication using an ultrasonic probe (2 sec, twice), total RNA was extracted according to the manufacturer's instructions. Approximately 5–10 µg of total RNA was recovered in 50 µl of water. In some experiments, RNA was prepared from psoriatic scales using essentially the same procedure. Thirty microliter aliquots of RNA were used in 50 µl reactions for first strand cDNA synthesis using either an oligo-dT-adaptor primer, random hexamer primers, or the Marathon RACE procedure (Clontech) as described previously (Brash et al. (1996) *J. Biol. Chem.* 271, 20549–20557). One microliter aliquots of cDNA were used directly in PCR reactions.

PCR Experiments

The primers encoded conserved sequences in animal and plant lipoxygenases. Two upstream primers encoded the sequence WLLAK (SEQ ID NO:5) from the middle of the lipoxygenase primary structure. This sequence forms the beginning of a long helix that crosses the center of the protein and includes two of the histidine iron ligands. The two upstream primers differed only in using alternative codons for the 3' lysine, AAA or AAG, and were designated as WLLAK-(AAA) and WLLAK-(AAG): 5'-GAC-GTC-TGG-YTi-YTi-GCi-AAA, (SEQ ID NO:6) or -AAG-3' (SEQ ID NO:7) (where i encodes inosine). The human 5S-lipoxygenase and the blood cell 15S-lipoxygenase are encoded as WLLAK-(AAA) (SEQ ID NO:6) (Matsumoto et al. (1988) *Proc. Natl. Acad. Sci. USA* 85; 26–30; Dixon et al. (1988) *Proc. Natl. Acad. Sci. USA* 85, 416–420; Sigal et al. (1988) *Biochem. Biophys. Res. Comm.* 157, 457–464), whereas the platelet 12-lipoxygenase uses WLLAK-(AAG) (SEQ ID NO:7) (Table 2) (Funk et al. (1990) *Proc. Natl. Acad. Sci. USA* 87, 5638–5642; Izumi et al. (1990) *Proc. Natl. Acad. Sci. USA* 87, 7477–7481). (One of the three papers on the human platelet 12-lipoxygenase reports a different sequence around this lysine, Yoshimoto et al. (1990) *Biochem. Biophys. Res. Comm.* 172, 1230–1235.)

For the first round PCR, each upstream primer was used in separate reactions against a set of downstream primers encoding an amino acid sequence that occurs seven amino acids downstream of the most 3' histidine ligand to the lipoxygenase iron on a second long helix. The sequence GQLDW (SEQ ID NO:8) occurs in the human 12S- and 15S-lipoxygenases beginning at amino acid position 546 and was encoded (with an additional three amino acids of consensus sequence on the 5' end) as 5'-CCA-AGT-GTA-CCA-RTC-NAG-YTG-NCC-3' (SEQ ID NO:9). The sequence GQYDW (SEQ ID NO:35) occurs in the equivalent position in the human 5S-lipoxygenase and this primer differed only in changing one amino acid code from leucine to tyrosine (5'-CCA-AGT-GTA-CCA-RTC-RTA-YTG-NCC-3') (SEQ ID NO:10).

The first round PCR reaction was primed with human hair follicle cDNA and in some experiments with cDNA prepared from psoriatic scales (1 μl from a 50 μl reaction using 5 μg total RNA) per 50 μl PCR reaction, and using 10 mM Tris, pH 8.3, 50 mM KCl, 3 mM MgCl$_2$ with 0.2 mM of each dNTP and 0.25 μl (1.25 units) AmpliTaq DNA polymerase (Perkin Elmer) in a Perkin Elmer 480 thermocycler. After addition of cDNA at 80° (hot start), the PCR was programmed as follows: 940 for 2 min, 1 cycle; 50° for 1 min, 72° for 1 min, 94° for 1 min, 30 cycles; 72° for 10 min, 1 cycle, and then the block temperature was held at 4° C.

For second round PCR, the upstream primer was either retained as before (WLLAK-(AAA) (SEQ ID NO:6) or WLLAK-(AAG) (SEQ ID NO:7)), or changed to a nested upstream primer modified very slightly from that used by Funk and colleagues (Funk et al. (1990) *Proc. Natl. Acad. Sci. USA* 87:5638–5642) for cloning of the human 12S-lipoxygenase and encoding the sequence XVDWLLAKX-WVR (SEQ ID NO:36): 5'-TA-GTC-GAC-TGG-CTT-YTG-GCC-AAA-iiC-TGG-GTS-CG-3' (where S ("strong") encodes C or G) (SEQ ID NO:11). The downstream primer for all second round reactions (nested PCR) encoded the sequence ELQXWWR (SEQ ID NO:26) and included a BamHI restriction site at the 5' end: 5'-G-CGG-ATC-CCT-CCA-CCA-GGN-YTG-SAG-YTC-3' (SEQ ID NO:12). The second round PCR reactions used 1 μl of 10-times dilute first round PCR products as cDNA and otherwise the conditions differed only in using either 55° or 58° as annealing temperature.

3' RACE and 5' RACE

The 3' sequence was obtained using established upstream sequence for the new human lipoxygenase (first round: 5'-GGT-ATC-TAC-TAC-CCA-AGT-GAT-GAG-3' (SEQ ID NO:13); second round: 5'-TAC-CCA-AGT-GAT-GAG-TCT-GTC-3' (SEQ ID NO:14)) against a downstream primer based on the adaptor-linked oligo-dT primer used for cDNA synthesis, as described previously (Brash et al. (1996) *J. Biol. Chem.* 271:20549–20557). The 5' RACE was accomplished using the Marathon cDNA Amplication Kit (Clontech) (Brash et al. (1996) *J. Biol. Chem.* 271:20549–20557) using 4 μg of total RNA from beard hair follicles. The gene-specific downstream primers were 5'-GAA-GAC-CTC-AGG-CAG-CAG-ATG-TG-3' (SEQ ID NO:15) and 5'-TC-ATG-GAA-GGA-GAA-CTC-GGC-AT-3' (SEQ ID NO:16). A full length clone was obtained by PCR using primers purified by HPLC (Brash et al. (1996) *J. Biol. Chem.* 271:20549–20557) and using a proof-reading mixture of Taq/Pwo DNA polymerases (Expand High Fidelity, Boehringer-Mannheim) as described (Brash et al. (1996) *J. Biol. Chem.* 271:20549–20557). The upstream primer encoded the N-terminus with a BamHI site added at the 5' end to facilitate subcloning: 5' AC-GGA-TCC-AGC-ATG-GCC-GAG-TTC-AGG-GTC-AG 3' (SEQ ID NO:17), and the downstream primer encoded the C-terminus of the protein with an added 5'EcoRI site to facilitate subcloning: 5' CGG-AAT-TCA-TGT-CAT-CTG-GGC-CTG-TGT-TCC 3' (SEQ ID NO:18). After a hot start at 80° C., the reaction conditions were 94°, 2 min, 1 cycle; 58° for 30 sec, 72° for 1 min 30 sec, 96° 15 sec, 3 cycles; 68° for 2 min, 96° 15 sec, 30 cycles; 72° 10 min, 1 cycle; hold at 4° C.

Northern Analysis

Two nylon membranes containing MRNA from human tissues (Clontech, Palo Alto, Calif.) were probed using a $^{32}$P-labeled 1059 bp fragment of the new human lipoxygenase prepared from the plasmid by PCR (with primers 5'-TG-CCT-CTC-GCC-ATC-CAG-CT-3' (SEQ ID NO:19) and 5' TG-TTC-CCC-TGG-GAT-TTA-GAT-GGA-3') (SEQ ID NO:20) and labeled by Rediprime random priming (Amersham). After hybridization in ExpressHyb solution (Clontech) at 68° C. for 1 hr, the membranes were washed finally in 0.1×SSC/0.1% SDS at 50° C. for 40 min and exposed to film.

Detection of the cDNA in Human Cornea

RNA was prepared using Tri Reagent (Molecular Research Center, Inc., Cincinnati, Ohio) from corneal epithelial cells scraped from eye bank corneas unsuitable for transplantation. The RNA samples were treated with DNAse 1, then reverse transcribed to cDNA. PCR reactions were run with human cornea CDNA as template, and also with rabbit cornea CDNA and buffer alone as negative controls. Additional negative controls using RNA without the reverse transcriptase step confirmed the absence of DNA contaminants in the samples. Two pairs of primers were used: GGT-ATC-TAC-TAC-CCA-AGT-GAT-GAG (SEQ ID NO:21) with 5'-TGGGATGTCATCTGGGCCTGT-3' (SEQ ID NO:22) giving a 589 bp product (#1), and from the 3' untranslated region (UTR), #2: 5'-AACTCACCCCCACCACCATACACA-3' (SEQ ID NO:23) with 5'-TTCCCGCCTCCATCTCCCAAAGT-3' (SEQ ID NO:24) giving a 351 bp product (# 2). Both reactions were run using an annealing temperature of 65° in the PCR. Northern analysis of eye tissues used approximately 1 μg of poly A-selected RNA and the same hybridization protocol as given above.

DNA Sequencing

PCR products were subcloned into the pCR2.1 vector (Invitrogen) and sequenced using the Oncor Fidelity manual dideoxy chain termination method or by automated sequencing on a ABI Prism 310 Genetic analyzer and fluorescence-tagged dye terminator cycle sequencing (Perkin Elmer).

Expression of cDNA, HPLC Analysis of Lipoxygenase Metabolism

The PCR products corresponding to the open reading frame of the cDNA were subcloned into the pCDNA3 vector (Invitrogen), or in some experiments ligated directly into pCR3 (Invitrogen), and expressed by transient transfection in human embryonic kidney (HEK) 293 cells as described (Funk et al. (1996) *J. Biol. Chem.* 271, 23338–23344). Following incubation with substrate (100 µM [1-$^{14}$C] arachidonic acid or [1-$^{14}$C]linoleic acid) for 30 min at 37° C., products were extracted using the Bligh and Dyer procedure (Bligh et al. (1959) *Can. J. Biochem. Physiol.* 37:911–917) and the extracts were analyzed by reversed-phase HPLC, straight phase HPLC and chiral column analysis (Brash et al. (1990) *Method. Enzymol.* 187:187–192).

Results of PCR Experiments

As described more fully in Experimental Procedures and summarized in Table 2, a PCR strategy was developed using sets of degenerate upstream and downstream primers that would resolve the known 5S-, 12S-, and 15S-lipoxygenases into separate tubes. The reactions were run under non-stringent conditions to permit detection of related sequences. After two rounds of reactions (nested PCR, see Experimental Procedures), successful amplification was expected to give a PCR product of approximately 500 bp.

When the reactions were carried out using different human hair root cDNAs as template, bands of ≈500 bp were evident in tubes corresponding to several of the original combinations of primer. Many of the bands were found to represent the known 12S- and 15S-lipoxygenase sequences. These two cDNAs were successfully resolved into separate PCR reactions by making use of their different codon usages for lysine 344 at the 3' end of the upstream primer (Table 2, and Experimental Procedures). Over 60 clones from the first two primer combinations in Table 2 were categorized as 12- or 15-lipoxygenase by sequencing and/or restriction enzyme digest with ApaI and HindIII.

Particular attention was paid to the 500 bp product obtained from the fourth primer set in Table 2, as this combination of sequences is not found in the three previously cloned human lipoxygenases. Of 41 clones with the correct sized insert, 39 cut with ApaI as expected of the human 12S-lipoxygenase. These clones appeared to correspond to 12S-lipoxygenase cDNA that had annealed to the slightly mismatched primers under the non-stringent conditions of PCR; a limited number were sequenced and all were identical to the human 12S-lipoxygenase. Two of the 41 positive clones did not cut with ApaI or HindIII, and sequencing indicated these clones represented a new lipoxygenase cDNA. The complete cDNA sequence of this new lipoxygenase was extended by 3' RACE and 5' RACE, and full length clones corresponding to the open reading frame were obtained by PCR. Two of the active clones (see below) were fully sequenced. The percent identity to the reported amino acid sequences of the 5S-, 12S- and 15S-lipoxygenases are approximately 44% to the 5-lipoxygenase, and 38–39% to the 12- and 15-lipoxygenases. FIG. 1 shows the deduced amino acid sequence (SEQ ID NO:1) in alignment with the 15S-lipoxygenase of human blood cells (SEQ ID NO:25) (Sigal et al. (1988) *Biochem. Biophys. Res. Comm.* 157, 457–464).

Results of Expression Studies

Initially, five full length clones were expressed in HEK 293 cells and the lipoxygenase activity evaluated by incubation with [$^{14}$C]arachidonic acid followed by HPLC analysis. Three of the PCR clones expressed with equivalent activity. The active clones made a single product, identified as 15-HETE (after reduction of the HPETE) on the basis of its retention time on reversed-phase HPLC (FIG. 2A) and SP-HPLC, and its characteristic uv spectrum (Ingram et al. (1988) *Lipids* 23:340–344); it was exclusively the 15S enantiomer as determined by chiral column analysis (FIG. 2B). The same product was formed following expression in Hela cells and Cos cells, and in these experiments another twenty clones, eight active, were evaluated. Addition of calcium (2 mM) or ATP (2 mM) to the incubation media had no significant effect on enzymatic activity.

Differences from the 15S-lipoxygenase of Blood Cells

Applicants looked carefully for any 12-HETE or other HETE by-products of the new 15S-lipoxygenase and unexpectedly, found none. This is in sharp contrast to the 15S-lipoxygenase of human blood cells that was analyzed in the same experiments; as reported before, the blood cell 15S-lipoxygenase forms 10–20% 12S-HETE in addition to 15S-HETE (Bryant et al. (1982) *J. Biol. Chem.* 257:6050–6055).

A comparison of the metabolism of arachidonic acid and linoleic acid revealed a second significant difference between the two enzymes. Linoleic acid is an excellent substrate for the blood cell 15S-lipoxygenase (Soberman et al. (1985) *J. Biol. Chem.* 260:4508–4515); in applicants' experiments it was metabolized more extensively than arachidonic acid. Although the new 15-lipoxygenase did metabolize linoleic acid, it was not as good a substrate. In two experiments, linoleic acid was 11% and 37% metabolized by the new enzyme, while the respective values for arachidonic acid were 30% and 83% conversion.

Expression in Other Tissues

Figure 3A:
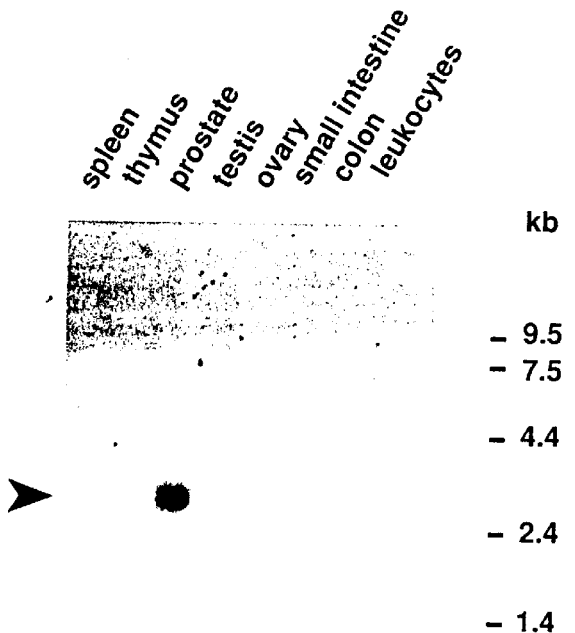
FIGS. 3A and 3B shows multiple human tissue RNA blots. Two tissue blots of mRNA (Clontech) were probed with a 1067 bp fragment of the new human lipoxygenase cDNA.
Figure 3B:
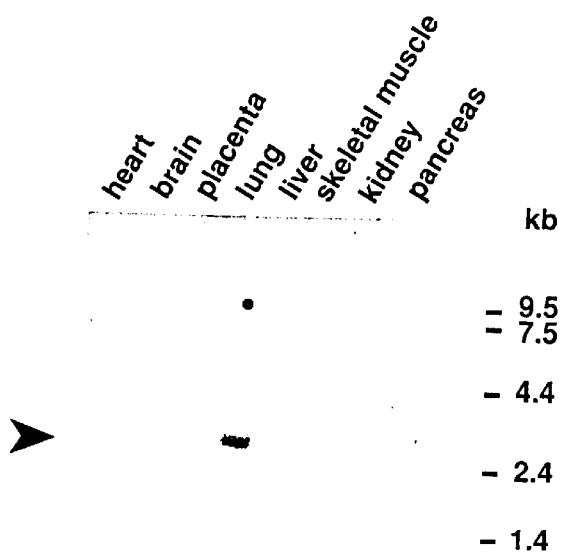
Figure 4A:
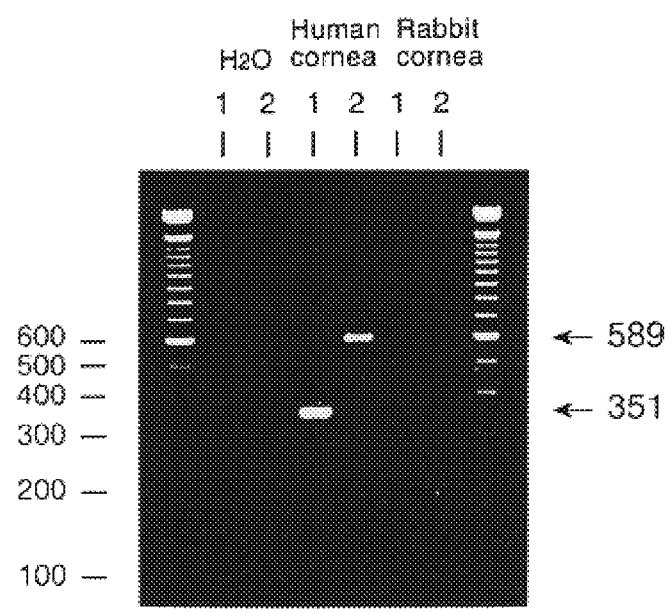
FIGS. 4A–B show detection of the new 15S-lipoxygenase transcript in human cornea.
Figure 4B:
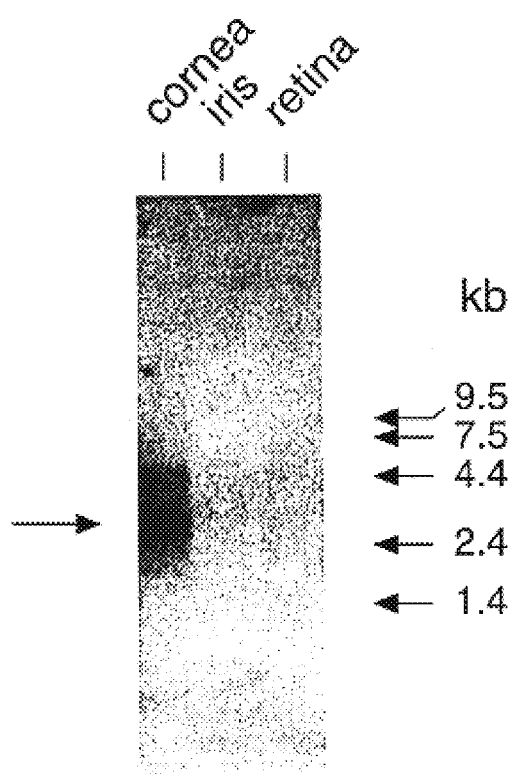

Multiple tissue Northern blots showed fourteen tissues negative for the new 15S-lipoxygenase mRNA (heart, brain, placenta, liver, skeletal muscle, kidney, pancreas, spleen, thymus, testis, ovary, small intestine, colon, and peripheral blood leukocytes) and two distinctly positive (FIG. 3). The positive tissues, lung and prostate, showed a transcript estimated as 2.5–3 kb, compatible with the established size of the cDNA (2.7 kb). Applicants also checked for the presence in cornea (originally because of a suspected connection to 12R-HETE synthesis). As determined by RT-PCR, human cornea is positive for the new lipoxygenase mRNA (FIG. 4a), and Northern analysis confirmed the presence of the new lipoxygenase transcript (FIG. 4b).

The human lipoxygenases can be distinguished by their positional specificity, by other distinctive features of their catalytic activities such as their ability to metabolize Cie fatty acid substrates, by their cellular distribution, and functionally, in their physiological roles. Funk, C. D. (1993) *Prog. Nuc. Acid Res. Mol. Biol.* 45:67–98. The new 15S-lipoxygenase characterized herein has a distinctive substrate specificity, a unique tissue distribution, and a different physiological role from the previously known human 15S-lipoxygenase.

The primary structure of the new enzyme has the features typical of a lipoxygenase. It has about 40% amino acid sequence identity to the blood cell 15S-lipoxygenase and other reported mammalian lipoxygenases. The sequence contains the absolutely conserved iron-binding histidines and the carboxy terminal isoleucine that also functions as an iron ligand (Boyington et al. (1993) *Science* 260:1482–1486; Minor et al. (1996) *Biochemistry* 35:10687–10701). One difference from other members of the lipoxygenase gene family is a change in the putative fifth iron ligand, normally a histidine or asparagine (N693 in the soybean L1 enzyme (Boyington et a!. (1993) *Science* 260:1482–1486; Minor et al. (1996) *Biochemistry* 35:10687–10701), H544 in the human blood cell 15S-lipoxygenase (Sigal et al. (1988) *Biochem. Biophys. Res. Comm.* 157:457–464). In the new human lipoxygenase the equivalent residue is changed to a serine (S557).

Catalytically the enzyme differs from the blood cell iSS-lipoxygenase in two important respects: it oxygenates more exclusively at the 15 carbon, and linoleic acid is a relatively poor substrate. These two features of the new 15S-lipoxygenase, the high positional specificity and the preference for arachidonic acid, have a parallel among 12-lipoxygenases in the properties of the 12S-lipoxygenase of platelets (Nugteren, D. H. (1975) *Biochim. Bikophys. Acta* 380:299–307;Hada et al. (1991) *Biochim. Biophys. Acta* 1083:89–93). Given this analogy in catalytic activities, it is likely that the new enzyme will be a comparatively poor metabolizer of esterified fatty acids, in contrast to the blood cell 15S-lipoxygenase (Schewe et al. (1975) *FEBS Lett.* 60:149–153; Murray et al. (1988) *Arch. Biochem. Biophys.* 265:514–523).

The four tissues in which the new enzyme is located, skin, lung, prostate and cornea, are all reported sites of 15-HETE synthesis. In human skin, applicants have now established the occurrence of both types of 15S-lipoxygenase. In lung, the 15-HETE synthesis has been ascribed to the blood cell type of 15-lipoxygenase (Sigal et al. (1992) *Am. J. Physiol.* 262:L392–398) and this enzyme has been detected by immunohistochemistry (Nadel et al. (1991) *J. Clin. Invest.* 87:1139–1145; Shannon et al. (1991) *Am. J. Physiol.* 261:L399–405; Shannon et al. (1993) *Am. Rev. Respir. Dis.* 147:1024–1028). But, clearly the possibility that the new 15-lipoxygenase contributes to the synthesis in certain cell types should be re-examined. Applicants' finding of the mRNA in prostate is compatible with the reports by Oliw and colleagues of the occurrence of 15-lipoxygenase in prostasomes, components of semen secreted by the prostate gland. Oliw et al. (1989) *Biochim. Biophys. Acta* 1002:283–291; Oliw et al. (1993) *J. Reprod. Fertil.* 99, 195–199. Similarly, our detection of the cDNA in cornea is in accord with metabolism studies by Oliw and coworkers; they established that human cornea synthesizes 15S-HETE from [$^{14}$C]arachidonic acid. Liminga et al. (1994) *Biochim. Biophys. Acta* 1210:288–296. Additional studies using immunohistochemistry indicated expression of the blood cell type of 15S-lipoxygenase in human cornea. Liminga et al. (1994) *Exp. Eye Res.* 59, 313–321. In cornea, as in skin, it is likely that both types of 15S-lipoxygenase are expressed.

It appears that this enzyme is a lipoxygenase specific for certain epithelial tissues. Based on the Northern result on colon and small intestine, the enzyme is not expressed in all epithelia, but the tissues in which it is identified so far are epithelial or have a significant epithelial component. As described in Example 2, the new human enzyme is related in primary structure to the phorbol ester inducible 8S-lipoxygenase of mouse skin. Thus, regulation of the expression of the new human enzyme is a significant feature of its involvement in the pathophysiology of skin and other tissues.

TABLE 2

Primers (first round PCR) to resolve human lipoxygenases

| Upstream Primer | Downstream Primer[a] | Match to known lipoxygenase | Reference for known lipoxygenase |
|---|---|---|---|
| WLLAK-(AAA) (SEQ ID NO:6) | GQLDW (SEQ ID NO:8) | 15S-lipoxygenase | Sigal et al. (1988) |
| WLLAK-(AAG) (SEQ ID NO:7) | GQLDW (SEQ ID NO:8) | 12S-lipoxygenase | Funk et al. (1990); Izumi et al. (1990) |
| WLLAK-(AAA) (SEQ ID NO:6) | GQYDW (SEQ ID NO:35) | 5S-lipoxygenase | Matsumoto et al. (1988); Dixon et al. (1988) |
| WLLAK-(AAG) (SEQ ID NO:7) | GQYDW (SEQ ID NO:35) | NONE | NONE |

[a]All second round PCR reactions used the nested primer ELQXWWR (SEQ ID NO:26 and SEQ ID NO:12) described in Experimental Procedures.

EXAMPLE 2

Molecular Cloning and Functional Expression of a Phorbol Ester-Inducible 8S-Lipoxygenase (8-Lox) from Mouse Skin As described above, in the course of studies on HETE synthesis in skin, a second type of 15S-lipoxygenase from human skin was cloned. This enzyme is different from the well known reticulocyte-type of 15S-lipoxygenase in that it oxygenates arachidonic acid purely at C-15 and linoleic acid is a relatively poor substrate. Continuing with the abbreviations adopted above, the reticulocyte-type of 15S-lipoxygenase is referred to as 15-Lox-1 and the enzyme that is an aspect of this instant invention is referred to as 15-Lox-2 in this example.

It was not clear a priori what is the animal homologue of the new human lipoxygenase, 15-Lox-2. In searching for a potential murine homologue a series of PCR reactions using mouse skin were performed. This led to the detection of a new mouse cDNA that is characterized in this example.

One of the effects of topical application of phorbol ester to mouse skin is the induction of an 8S-lipoxygenase in association with the inflammatory response. This example describes the molecular cloning and characterization of this enzyme. The cDNA was isolated by PCR from mouse epidermis and subsequently from a mouse epidermal cDNA library. The cDNA encodes a protein of 677 amino acids with a calculated molecular weight of 76 kDa. The amino acid sequence has 78% identity to 15-Lox-2, and approximately 40% to other mammalian lipoxygenases. When expressed in vaccinia virus-infected Hela cells, the mouse enzyme converts arachidonic acid exclusively to 8S-hydroperoxyeicosatetraenoic acid, while linoleic acid is converted to 9S-hydroperoxy-linoleic acid in lower efficiency.

Phorbol ester treatment of mouse skin is associated with strong induction of 8S-lipoxygenase mRNA and protein. By Northern analysis, expression of 8S-lipoxygenase mRNA was also detected in brain. Immunohistochemical analysis of phorbol ester-treated mouse skin showed the strongest reaction to 8S-lipoxygenase in the differentiated epidermal layer, the stratum granulosum. The inducibility of this enzyme is likely a characteristic feature of the mouse 8S-lipoxygenase and its human 15S-lipoxygenase homologue.

Preparation of Mouse Epidermal Total RNA, and cDNA Synthesis

Phorbol ester (PMA, 10 nmol) dissolved in 50 ml of acetone was applied topically onto dorsal skin of 6–7-day-old mice. At 21–24 h after PMA-treatment, the mice were euthanized, and epidermis was prepared from the frozen dorsal skin as previously described (Hughes et al. (1991) *Biochim. Biophys. Acta* 1081:347–354). The frozen epidermis was dropped into guanidinium thiocyanate solution, the lysis buffer from the RNeasy RNA extraction kit (QIAGEN). After a brief sonication using an ultrasonic probe (2 sec, twice), total RNA was extracted according to the manufacturer's instructions. Approximately 50 mg of total RNA was recovered in 50 ml of water. Twenty microliter aliquots were used in 50 ml reactions for first strand cDNA synthesis using an oligo-dT-adaptor primer (Brash et al. (1996) *J. Biol. Chem.* 271:20949–20957). One microliter aliquots of CDNA were used directly in PCR reactions.

PCR Cloning of Epidermal Lipoxygenase cDNA—Initial PCR Clone

Two upstream degenerate primers encoded the sequence DVWLLAK (SEQ ID NO:27). The two primers differed only in using alternative codons for the 3' lysine, AAA or AAG, and they are referred to as WLLAK-(AAA) (SEQ ID NO:6) and WLLAK-(AAG) (SEQ ID NO:7). For the first round PCR reaction, each upstream primer was used in separate reactions against a set of downstream primers encoding three amino acid sequences beginning GQ that occur seven amino acids downstream of the most 3' histidine ligand to the iron: the sequence GQLDW (SEQ ID NO:8) occurs in mammalian 12S- and 15S-lipoxygenases, GQYDW (SEQ ID NO:35) occurs in 5S-lipoxygenases, and GQFDS (SEQ ID NO:28) occurs in the new human 15S-lipoxygenase, 15-Lox-2. The primer sequences are the same as those described in Example 1 above, except for the new degenerate downstream primer encoding GQFDS (SEQ ID NO:28): 5'-CCA-AGC-GCA-SSA-RTC-RAA-YTG-NCC (where S, "strong", encodes C or G) (SEQ ID NO:29). For the second round nested PCR reaction, the upstream primer was retained as before [WLLAK-(AAA) (SEQ ID NO:6) or WLLAK-(AAG) (SEQ ID NO:7)], while the downstream primer was changed in all reactions to encode the sequence ELQXWWR (SEQ ID NO:26). After the second round PCR, only the reaction that originally used the WLLAK-(AAG) (SEQ ID NO:7) and GQFDS primers (SEQ ID NO:29) yielded a visible PCR product. This product was 500 bp in size. The first round PCR reaction was primed with cDNA from phorbol ester-treated mouse epidermis, 1 ml per 50 ml PCR reaction (from a 50 ml cDNA synthesis using 20 mg total RNA), and using 10 mM Tris, pH 8.3, 50 mM KCl, 3 mM $MgCl_2$ with 0.2 mM of each dNTP and 0.25 ml (1.25 units) of AmpliTaq DNA polymerase (Perkin Elmer) in a Perkin Elmer 480 thermocycler. After the addition of the cDNA at 80° C. (hot start), the PCR was programmed as follows: 94° C. for 2 min, 1 cycle; 50° C. for 1 min, 72° C. for 1 min, 94° C. for 1 min, 30 cycles; 72° C. for 10 min, 1 cycle, and then the block temperature was held at 4° C. The second round reaction was primed with the equivalent of 0.1 ml of the first round reaction products (added as a 10-fold dilution). The protocol was 94° C. for 2 min, 1 cycle; 58° C. for 1 min, 72° C. for 1 min, 94° C. for 1 min for 30 cycles; the protocol was completed with one cycle at 72° C. for 10 min, and then the block temperature was held at 4° C.

3'-RACE and 5'-RACE

The 3' sequence was obtained using established upstream sequence 5' G-AGC-TTT-GTC-TCT-GAA-ATA-GTC-AG 3' (SEQ ID NO:30) against a downstream primer based on the adaptor-linked oligo-dT primer used for CDNA synthesis (Brash et al. (1996) *J. Biol. Chem.* 271:20949–20957). The 5' RACE was accomplished using a kit from GIBCO BRL according to the manufacturer's instructions. The gene-specific downstream primers were 5' GTG-AGG-AAT-CAA-TAG-CTT-GAA-GAG 3' (SEQ ID NO:31), and 5' G-ATG-TGT-GAC-AGC-CTC-ATG-GAT-G 3' (SEQ ID NO:32).

Full-length Clones Obtained by PCR

The upstream primer encoded the N-terminus with a HindIII site added at the 5' end to facilitate subcloning: 5' C-AAG-CTT-AGG-AGG-ATG-GCG-AAA-TGC-AGG 3' (SEQ ID NO:33), and the downstream primer encoded the C-terminus of the protein with an added 5'EcoRI site: 5' G-GAA-TTC-ATG-TTA-GAT-GGA-GAC-ACT-GTT 3' (SEQ ID NO:34). These two primers were is purified by HPLC with the DMT protecting groups on (Brash et al. (1996) *J. Biol. Chem.* 271:20949–20957). After deprotection they were used in PCR reactions with a proof-reading mixture of Taq/Pwo DNA polymerase (Expand High Fidelity, Boehringer-Mannheim) according to the manufacturer's instructions. The reaction conditions were 94° C., 2 min, 1 cycle; 58° C. for 30 sec, 72° C. for 1 min 30 sec, 96° C. for 15 sec, 3 cycles; 68° C. for 2 min, 96° C. 15 sec, 30 cycles; 72° C. for 10 min, 1 cycle; hold at 4° C.

DNA Sequencing cDNAs were sequenced using the Oncor Fidelity manual dideoxy chain termination method or by automated sequencing on a ABI Prism 310 Genetic analyzer and fluorescence-tagged dye terminator cycle sequencing (Perkin Elmer).

HPLC Analysis of Tipoxygenase Metabolism

The lipoxygenase metabolism of $[1-^{14}C]$arachidonic acid or $[1-^{14}C]$linoleic acid was evaluated essentially as described previously (Hughes et al. (1991) *Biochim. Biophys. Acta* 1081:347–354). Following incubation with 100 mM of substrate, products were extracted using the Bligh and Dyer procedure (Bligh et al. (1959) *Can. J. Biochem. Physiol.* 37:911–917), and the extracts were analyzed by RP-HPLC, SP-HPLC and chiral column analysis (Brash et al. (1990) *Methods Enzymol.* 187:187–192). The hydroperoxide products were reduced with triphenylphosphine, methylated with diazomethane, purified by SP-HPLC, and then the stereochemistry was analyzed using a Chiralcel OD column.

Expression of Mouse 8s-Lipoxygenase Clones

The PCR products corresponding to the open reading frame of the cDNA were ligated directly into pCR3.1 (Invitrogen), and expressed by transient transfection in HeLa cells using VTF-7, a recombinant vaccinia virus containing the T7 RNA polymerase gene (Blakely et al. (1991) *Anal. Biochem.* 194:302–308), or in human embryonic kidney (HEK) 293 cells using the adenovirus VA RNA gene. Funk et al. (1996) *J. Biol. Chem.* 271:23338–23344. In the former system, cells plated at $1\times10^6$ cells/35 mm well 48 h earlier were transfected with 1 mg of plasmid DNA and 3 mg of lipofectin, and harvested after 12 hours. In the HEK system, cells plated at $1\times10^6$ cells/10 cm dish 24 h earlier were transfected with 10 mg of plasmid DNA by the calcium phosphate method, and harvested after two to three (2–3) days. Funk et al. (1996) *J. Biol. Chem.* 271:23338–23344. The harvested cells were sonicated on ice, and the resulting homogenates were incubated with 100 mM $[1-^{14}C]$arachidonic acid or $[1-^{14}C]$linoleic acid for 45 min at room temperature. The metabolites were extracted and analyzed as described above.

Screening of cDNA Library

The library was a commercial 1 Unizap.XR skin cDNA library prepared using poly(A)+RNA isolated from whole skin of C57/Black female mice (Stratagene). It was screened with a 347 bp BsaMI fragment of the mouse 8S-lipoxygenase cDNA (PCR clone) as probe.

Northern Analysis

Poly(A)+RNA was prepared from PMA- or acetone-treated frozen dorsal skin using TRI REAGENT® (Molecular Research Center, Inc.) and Oligotex™ (Qiagen) according to the manufacturers' instructions. The poly(A)$^+$ RNA was electrophoresed in 1% agarose/formaldehyde gel and blotted to a Hybond-H$^+$ nylon membrane (Amersham). The membrane was hybridized with $^{32}$P-labeled DNA probe (complementary with a 0.6-kb EcoRV/BamHI fragment of mouse epidermal 8S-lipoxygenase) prepared using the Multiprime DNA labeling kit and Rapid-hybridization buffer (Amersham), and then washed according to the manufacturer's specifications. Blots were exposed to Fuji x-ray film at −80° C. Mouse cyclophilin cDNA was used as a housekeeping gene to access loading of RNA.

Western Analysis

After quantitation by Bradford assay (Bio-Rad), protein was separated by SDS polyacrylamide gel electrophoresis (SDS-PAGE) and then transferred electrophoretically to Hybond ECL nitrocellulose membranes (Amersham). These were probed using a rabbit polyclonal antibody raised against the human 15-Lox-2. This antibody recognises 15-Lox-2 and the mouse 8S-lipoxygenase, but not the human reticulocyte type of 15S-lipoxygenase, as more fully described below. Donkey anti-rabbit Ig linked with horseradish peroxidase (Amersham) was the secondary antibody. Specifically bound protein was detected by chemiluminescence using the ECL Western blotting detection reagents (Amersham).

Immunohistochemical Analysis

The dorsal and tail skin of six to seven (6–7)-day-old mice were treated with acetone or PMA (10 nmol for dorsal skin, 2 nmol for tail skin). After 24 h, the animals were euthanized and the dorsal and tail skin were washed with soap and then rinsed thoroughly with water. Whole dorsal and tail skin was immersion-fixed for 24 h in 4% paraformaldehyde in phosphate-buffered saline (pH 7.4), dehydrated in ethanolic solutions and xylenes, and embedded in paraffin. Skin sections were deparaffinized, rehydrated in graded alcohols. Endogenous peroxidase activity was blocked in 3% hydrogen peroxide/methanol for 20 min followed by incubation in 10% goat serum for 20 min. Sections were incubated at room temperature for 1 h in a ½500 dilution of either primary rabbit antisera that was used for Western analyses of 8S-lipoxygenase or pre-immune sera. After rinsing in PBS, sections were incubated with the biotinylated secondary antisera and peroxidase-labeled tertiary antisera supplied with an ABC Elite kit (Vector Corp, Guyrlingame, Calif.) followed by visualization of immunoprecipitate with DAB chromagen (Biogenix, Ban Ramon, Calif.).

Results of Molecular Cloning by RT-PCR

A series of PCR reactions were carried out with cDNA prepared from phorbol ester-treated mouse skin as template, and using degenerate primers based on well conserved sequences in mammalian lipoxygenases. The primers were identical to those used in the cloning of a novel 15S-lipoxygenase (15-Lox-2) from human skin as described in Example 1, with the addition of an extra downstream primer that better represented the sequence of the new human enzyme. After running the protocol of nested PCR reactions, a strong band of the expected size of 500 bp was obtained in one of the reactions that used the new downstream primer (see above for details). The sequence of this PCR product showed a striking homology to the human lipoxygenase sequence. The remainder of the mouse cDNA was cloned by conventional 3'- and 5'-RACE. cDNA corresponding to the open reading frame was prepared by PCR using a proof-reading mixture of Taq/Pwo as DNA polymerase. Eight of these clones were selected for expression studies. Seven clones were fully sequenced.

Figure 5A:
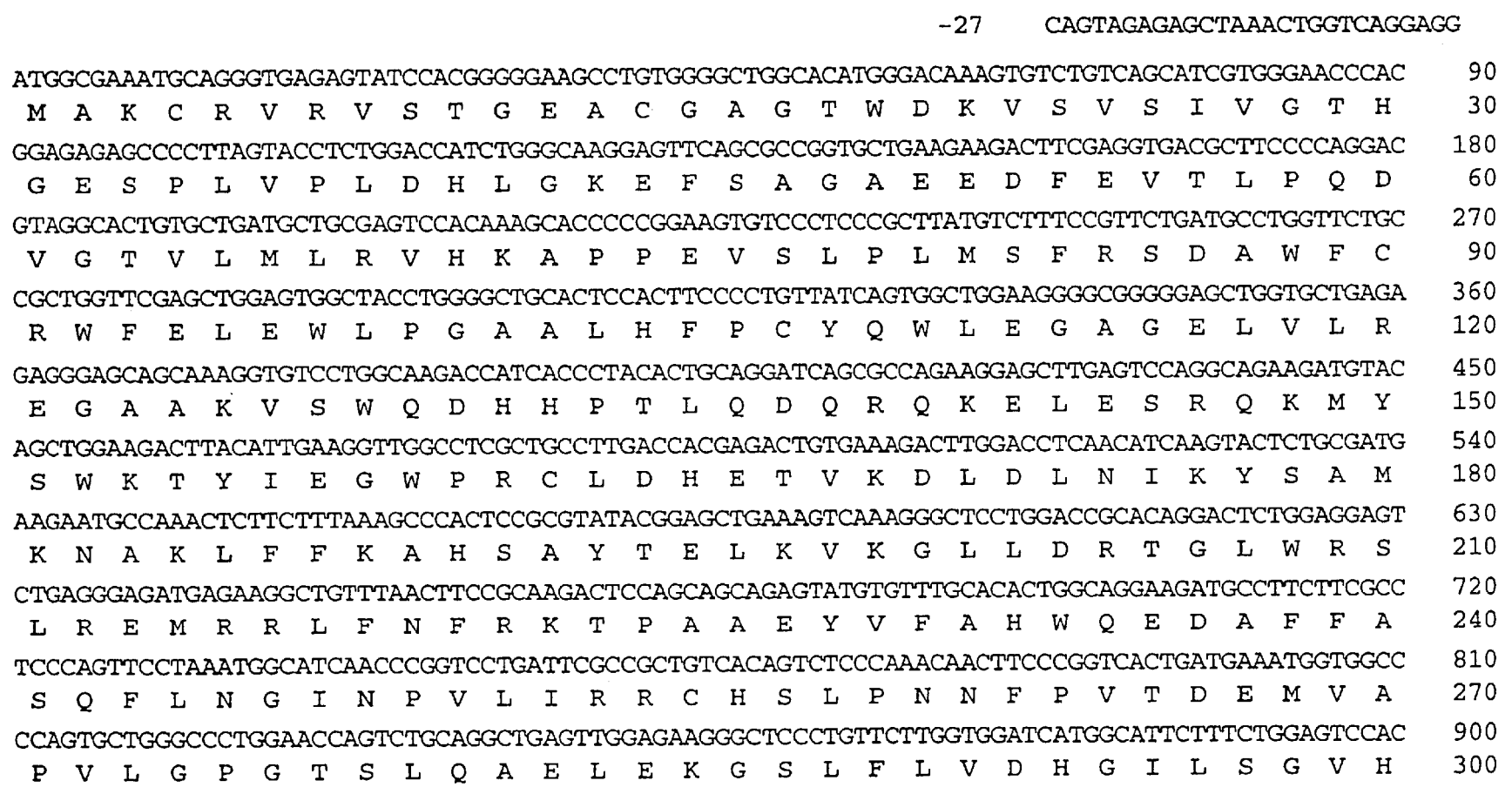
Figure 5B:
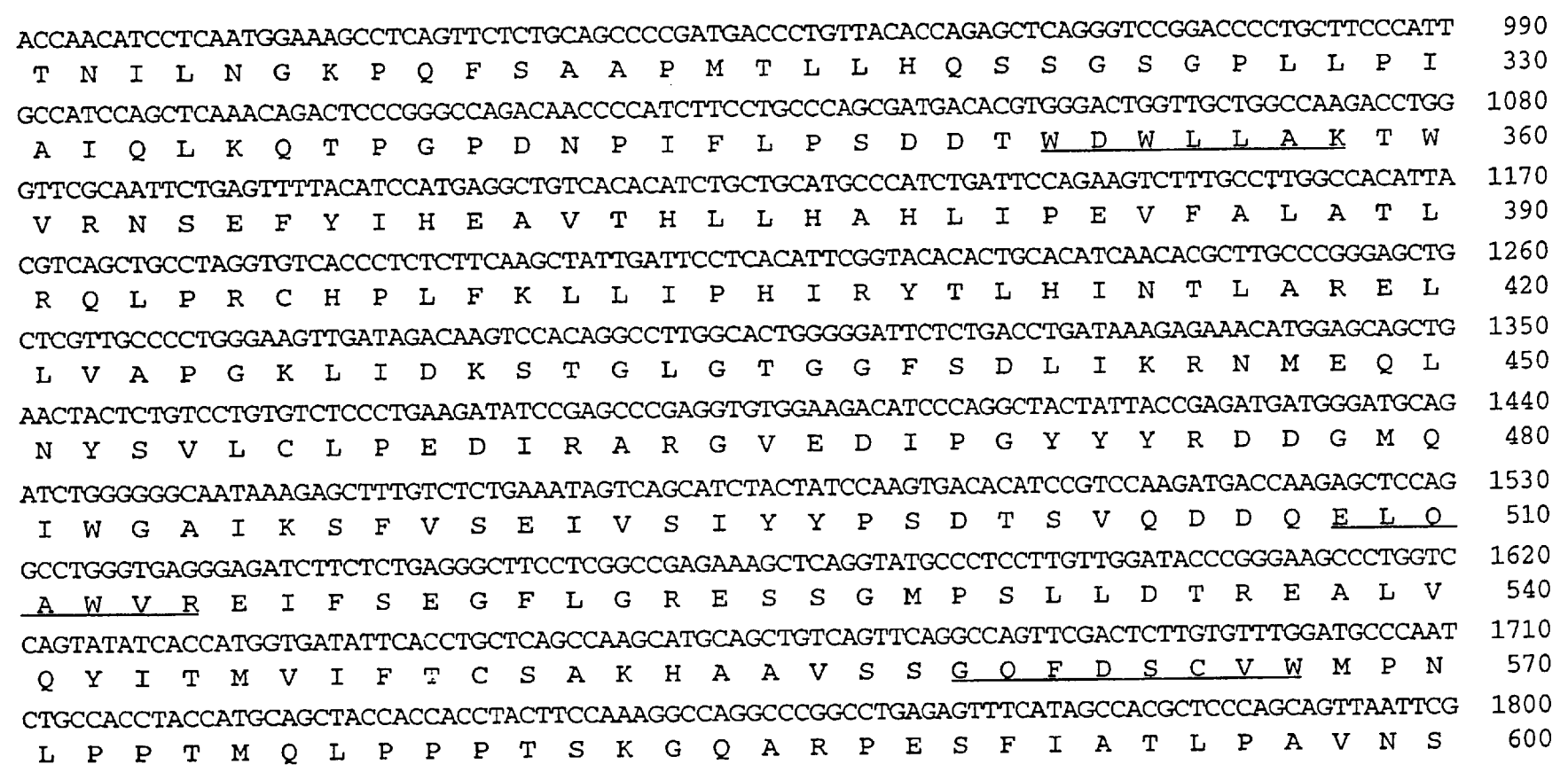
Figure 5C:
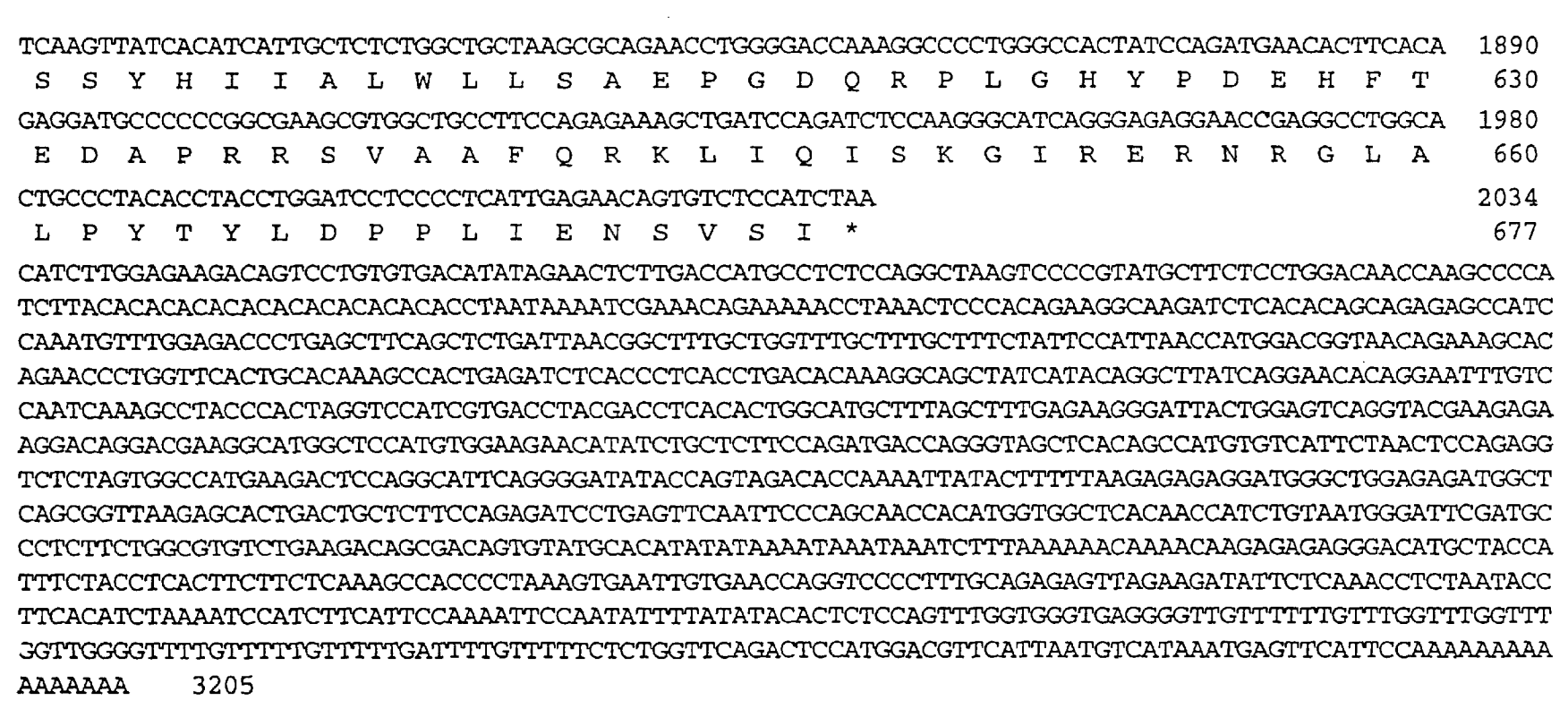

Subsequently, a partial cDNA sequence was used to screen a mouse skin cDNA library and two full length cDNAs of 3.2 kb were isolated and sequenced. These were identical to each other and also matched exactly one of the PCR products in the open reading frame (FIGS. 5A–5C). FIG. 6 shows an alignment with the human 15-Lox-2. The sequences are 78% identical at both the DNA and protein levels.

Transient Expression in HEK and Hela Cells

The library clone was obtained relatively late in this study, and therefore much of the expression work described here was carried out using several of the PCR products. It became apparent very early on that there is some problem in expression of this mouse lipoxygenase. Using a standard transient expression system in HEK 293 cells, it was only very occasionally that applicants detected enzymatic activity in the expressed mouse lipoxygenase. Positive controls using the human reticulocyte-type of 15S-lipoxygenase (15-Lox-1) or the second type of human 15S-lipoxygenase (15-Lox-2) were run in every experiment, and these cDNAs always expressed with readily detectible activity. In the few instances when active mouse lipoxygenase was obtained in HEK cell expression, the enzyme converted arachidonic acid to 8S-hydroperoxyeicosatetraenoic acid (8S-HPETE).

Figure 7A:
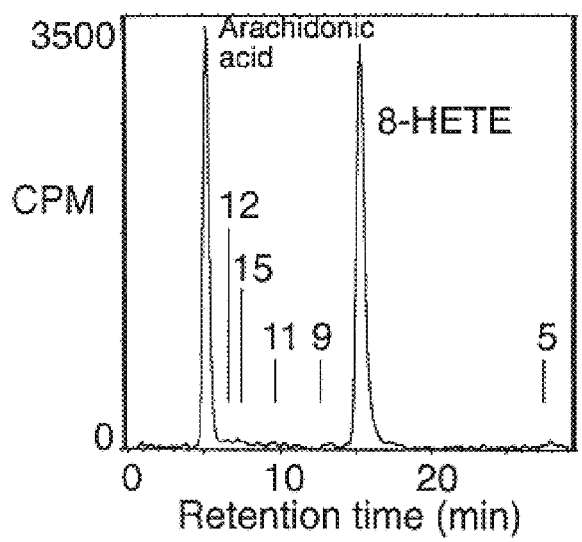
FIGS. 7A–C shows expression of 8S-lipoxygenase in vaccinia virus infected Hela cells. Cells sonicates were incubated with [1-$^{14}$C]arachidonic acid (100 µM) for 30 min at room temperature, then extracted with methylene chloride and treated with triphenylphosphine in methanol to reduce HPETEs to HETEs.
Figure 7B:
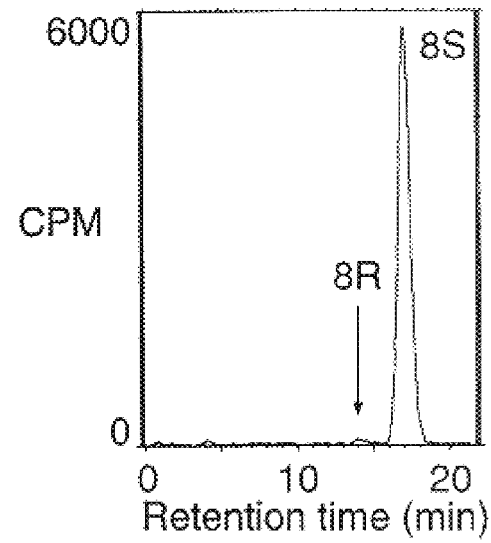

Consistent expression of the mouse skin lipoxygenase was obtained using HeLa cells infected with vaccinia virus encoding the T7 RNA polymerase. Blakely et al. (1991) *Anal. Biochem.* 194:302–308. In this system, using sonicated cells from a 35 mm well, typically 30–40% of added arachidonic acid (100 μM) was converted to 8S-HPETE as the sole enzymatic product (FIG. 7). The percentage conversion of arachidonic acid in this system was always similar to that obtained using the human 15-Lox-2 as a positive control. Active enzyme was obtained using several of the PCR clones (that encode one, two, or three different amino acids from the library clone, FIGS. 5A–5C description) and the library clone itself.

Figure 8A:
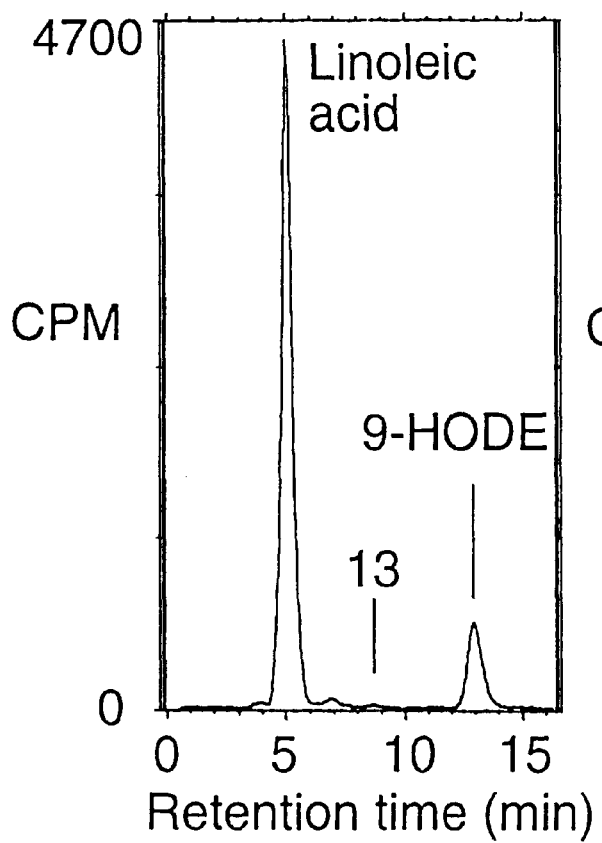
FIGS. 8A–B shows linoleic acid metabolism by 8S-lipoxygenase expressed in vaccinia virus-infected HeLa cells. Metabolism studies with [$^{14}$C]linoleic acid (100 µM) used the same incubation and analysis conditions as described in the legend to FIG. 7.
Figure 8B:
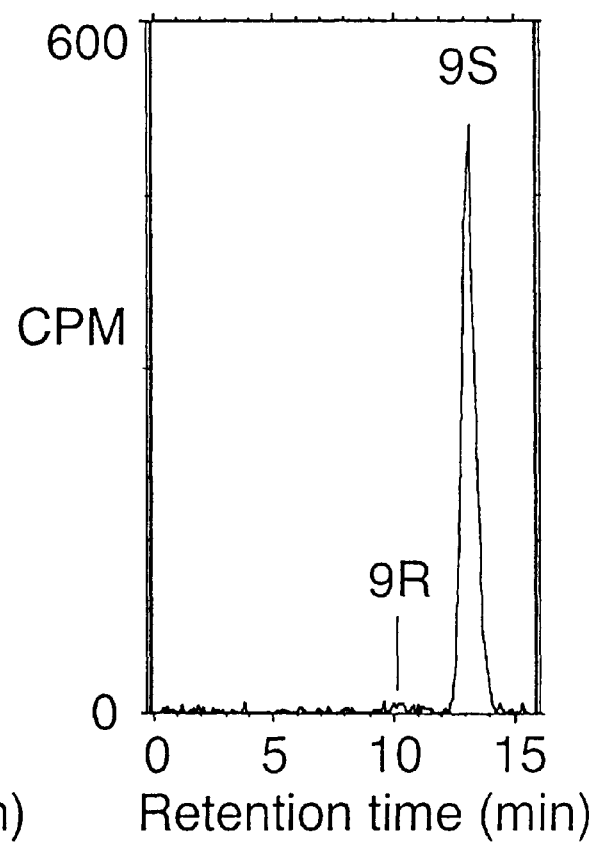

Using the vaccinia expression system, linoleic acid was found to be a substrate for the mouse 8S-lipoxygenase although the conversion was two to three (2–3)-fold lower compared to arachidonic acid. The enzyme converted linoleic acid exclusively to 9S-HODE (FIG. 8).

Effect of Phorbol Ester on Expression of 8S-Lipoxygenase in Mouse Skin

The expression level of 8S-lipoxygenase in mouse skin is known to be strongly strain-dependent. Fischer et al. (1987) *Cancer Res.* 47:3174–3179; Fischer et al. (1987) *Carcinogenesis* 8:421–424; Fischer et al. (1988) *Cancer Res.* 48:658–664. Also, the highest activity is inducible in six to ten (6–10)-day-old animals. Gschwendt et al. (1986) *Carcinogenesis* 7:449–455; Furstenberger et al. (1991) *J. Biol. Chem.* 266:15738–15745. Applicants examined several strains of mice and observed major differences in the level of constitutive expression (with no phorbol ester) and in the level after phorbol ester treatment. For example, using the Sencar strain applicants observed high constitutive 8S-lipoxygenase activity in six to ten (6–10)-day-old pups, with little extra induction by phorbol ester. The results shown here were obtained using a mixed breed of black Swiss animals that have low constitutive activity of 8S-lipoxygenase and exhibit strong induction with phorbol ester. Using six to ten (6–10)-day-old pups, the inducing effect of phorbol ester clearly is related to induction of both MRNA and protein (FIG. 9).

Cellular Localization of 8S-Lipoxygenase in Mouse Skin

The localization of mouse 8S-lipoxygenase protein in dorsal skin and tail skin was observed and characterized by immunohistochemical analysis. A thickened hyperproliferative epidermis after PMA treatment was observed. An increase in 8S-lipoxygenase is due to an expansion in cellularity in the stratum granulosum compartment of the epidermis. Baseline staining of the stratum granulosum for 8S-lipoxygenase in skin receiving vehicle alone(acetone) was performed. The absence of immunoreactivity after incubation of PMA treated skin with pre-immune antisera was also observed.

Thus, expression of the 8S-lipoxygenase protein was examined in normal mouse skin following treatment with phorbol ester in acetone (PMA) or acetone alone using the strain of black Swiss animals responsive to PMA. The histological analysis of skin from two differing body locations (thin dorsal skin and thick tail skin) revealed a marked hyperproliferative response to PMA and a diminished response to the acetone vehicle alone. Most notable was an increase in the number of differentiated cells within the outer epidermal compartment, the stratum granulosum. The net result was more 8S-lipoxygenase positive cells in the the PMA treated samples as compared to the samples receiving acetone alone. No immunoreactivity was detected in any samples reacted with pre-immune serum. Hair follicles positioned within the underlying dermis also showed positive staining for 8S-lipoxygenase in differentiated cell layers. Staining in these locations did not show a modulation in response to topical treatment with phorbol ester.

Tissue Distribution of 8S-Lipoxygenase

Figure 10:
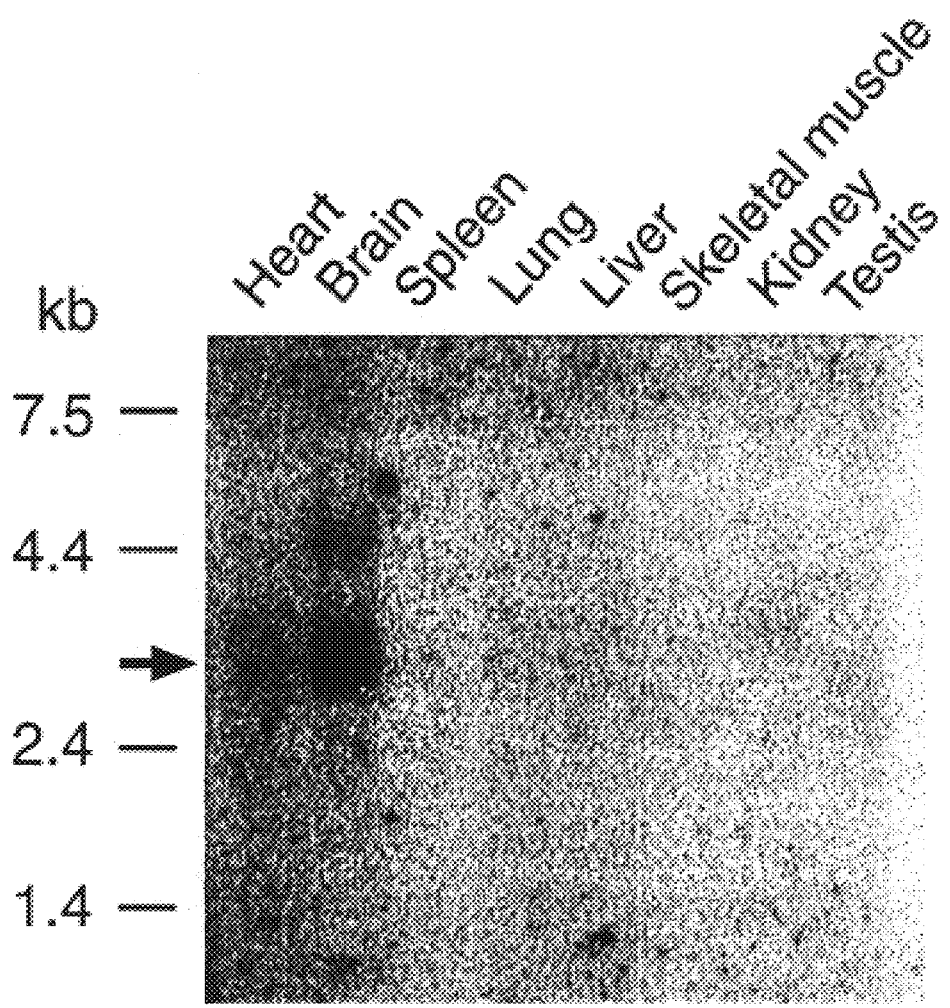
FIG. 10 shows multiple tissue Northern analysis of mouse 8S-lipoxygenase. A mouse tissue blot of mRNA (Clontech) was probed with a 618 bp EcoRV-BamHI fragment of 8S-lipoxygenase cDNA.

As the related human 15S-lipoxygenase, 15-Lox-2, is expressed in prostate, an activity assay was used (HPLC analysis of products formed from [1-$^{14}$C]arachidonic acid) to examine for 8S-lipoxygenase activity in mouse prostate. Using young adult males of 8 weeks of age, high levels of cyclooxygenase and 12S-lipoxygenase activities were found in the prostate, but no 8S-lipoxygenase products were detected. Occurrence of the 8S-lipoxygenase transcript was examined in several different tissues by Northern analysis. This revealed expression of 8S-lipoxygenase transcript in mouse brain, with no detectible expression in heart, spleen, lung, liver, skeletal muscle, kidney and testis (FIG. 10).

Mouse 8S-lipoxygenase cDNA was cloned by PCR using primers related to the characterized human 15S-lipoxygenase (15-Lox-2) also described herein. These two lipoxygenases have 78% amino acid identity, and the differences are mainly conservative substitutions. The two enzymes have 30–45% identity to other mammalian lipoxygenases. The primary structure of the mouse 8S-lipoxygenase contains the absolutely conserved iron-binding histidines of lipoxygenases and the C-terminal isoleucine that is also an iron ligand. Boyington et al. (1993) *Science* 260:1482–1486; Minor et al. (1996) *Biochemistry* 35:10687–10701. A notable feature of the mouse 8S-lipoxygenase primary structure is the presence of a serine at amino acid position 558 as the putative 5th iron ligand. Minor et al. (1996) *Biochemistry* 35:10687–10701. The equivalent residue in all other lipoxygenases is either a histidine or asparagine, with the exception of the human 15-Lox-2 in which a serine is also present. Based on the sequence similarity, the 8S-lipoxygenase is the mouse homologue of the human 15-Lox-2.

Initially, there was difficulty in studying the mouse enzyme as reliable expression of active lipoxygenase could not be obtained using a conventional HEK cell system. Chen et al. (1995) *J. Biol. Chem.* 270:17993–17999; Chen et al. (1994) *J. Biol. Chem.* 269:13979–13987. The problem was solved by use of the recombinant vaccinia virus in a co-transfection system in Hela cells. In this procedure, the cells are co-transfected with the plasmid cDNA and vaccinia virus encoding the T7 RNA polymerase. The virus protein induces high level expression via the T7 promoter upstream of the lipoxygenase CDNA. The cells are harvested after 12 hours. In this system, the mouse enzyme expressed with equivalent activity to either the 15-Lox-1 or 15-Lox-2 positive controls. Each of these lipoxygenases was expressed at a much higher level in the viral infected Hela cells than in the other procedure using the HEK cells.

Figure 7C:
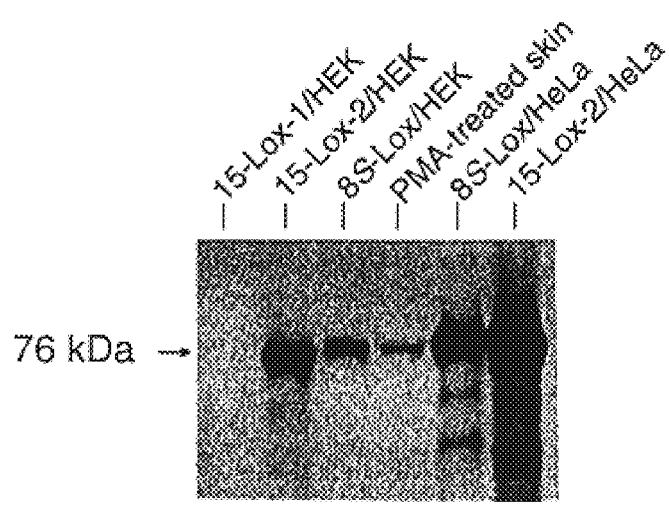

The Western results show clearly that HEK cells produce the 8S-lipoxygenase protein, although at lower levels than the positive controls (FIG. 7C). Whether this is a transfection problem, or related to translation or protein stability is not resolved. A similar poor expression of activity of the mouse epidermal-type of 12S-lipoxygenase was found in HEK cells. Funk et al. (1996) *J. Biol. Chem.* 271:23338–23344. The lipoxygenase proteins expressed in HEK and HeLa cells were indistinguishable in size by Western analysis. The very same preparations of 8S-lipoxygenase plasmid cDNAs that failed to express active 8S-lipoxygenase in HEK cells were expressed with good activity in the vaccinia system. Changing the vector from pCR3 to pCDNA3 had no effect on HEK cell expression. Extracts of Hela cells (+/− viral infection or vector alone) did not restore catalytic activity to HEK cells transfected with 8S-lipoxygenase. Furthermore, changing the vaccinia virus system over to HEK cells failed to induce expression of 8S-lipoxygenase, whereas a 15-Lox-2 positive control gave easily measureable 15S-lipoxygenase activity. HEK cells may lack some factor that helps the effective expression of certain lipoxygenase enzymes.

Linoleic acid was converted with about 3-fold lower efficiency than arachidonic acid by the 8S-lipoxygenase. It was, however, specifically oxygenated to 9S-HPODE and likely participates in the biosynthesis of this product in vivo. Linoleic acid is an abundant polyunsaturated fatty acid in mouse skin and thus, potentially, this substrate is available. Ziboh et al. (1988) *Prog. Lipid Res.* 27:81–105. Lehmann and colleagues noted that the levels of 8-HETE and 9-HODE in mouse skin tend to change in parallel. Both are strikingly elevated in mouse skin papillomas are lower than normal in skin carcinomas. Lehmann et al. (1992) *Anal. Biochem.* 204:158–170. The 9S chirality of the product from linoleic acid is one criterion that could be used to assess the contribution of the 8S-lipoxygenase to formation of 9-HODE in mouse skin. The main cyclooxygenase product from linoleic acid is the enantiomeric 9R-HODE (Hamberg et al. (1980) *Biochim. Biophys. Acta* 617:545–547), while non-enzymatic reactions would give racemic product.

Northern and Western analyses, as well as the activity assay, showed that PMA treatment strongly induced de novo synthesis of mouse 8S-lipoxygenase in the dorsal skin of the outbred mice used in this experiment. The histochemical analyses further defined the effect of PMA. Immunoreactive 8S-lipoxygenase protein was most prominent in a layer of differentiated epidermis, the stratum granulosum. The thickness of this cell layer increased markedly following 24 hours of treatment with PMA. An increase in the number of cells that produce 8S-lipoxygenase, therefore, is one of the causes of the increased 8S-lipoxygenase activity induced by PMA.

In the Northern analysis using a multiple tissue blot, 8S-lipoxygenase mRNA was detected clearly in brain, but not in the other seven tissues examined. Both the stratum granulosum of the epidermis and the neuronal tissues of the central nervous system were originally derived from the same ectodermal layer in early embryonic development, and both represent highly differentiated cell types. Occurrence of the 8S-lipoxygenase transcript in brain was unexpected as lipbxygenase-catalyzed formation of 8-HETE has not been reported in neuronal tissues. The negative reaction in liver is of interest in relation to the reported activity of 8S-HETE as a strong activator of the peroxisome proliferator-activated receptor, PPAR-a. Yu et al. (1995) *J. Biol. Chem.* 270:23975–23983. In liver, there is the possibility of synthesis of 8-HETE via the microsomal cytochrome P-450 system, although in vitro this gives a nearly racemic 8-HETE product. Capdevila et al. (1986) *Biochem. Biophys. Res. Commun.* 141:1007–1011.

The absence of 8S-lipoxygenase signal in the Northern analysis of liver, could, however, be related to the lack of induction in normal tissue. The same issue applies to the absence of detectible 8S-lipoxygenase activity in normal mouse prostate from young adult males. Although the human homologue of the mouse 8S-lipoxygenase, 15-Lox-2, was readily detectible in human prostate, as described in Example 1, the pooled human sample would include tissue from older subjects, the majority of which are expected to exhibit benign prostatic hyperplasia. Oesterling, J. E. (1996) *Prostate* 6:67–73. The induction of 8S-lipoxygenase in mouse skin by phorbol ester certainly is thus a striking feature of this enzyme.

REFERENCES

The references listed below as well as all references cited in the specification are incorporated herein by reference to the extent that they supplement, explain, provide a background for or teach methodology, techniques and/or compositions employed herein.

Adelman et al. (1983) *DNA* 2:183.
Ausubel, F. M., et al. *Current Protocols in Molecular Biology*, (J. Wylie & Sons, N.Y.), 1992.
Baden et al. (1979) *J. Amer. Acad. Dermatol.* 1:121–122.
Baer et al. (1991) *J. Lipid Research* 32:341–347.
Baer et al. (1993) *J. Lipid Research* 34:1505–1514.
Baer et al. (1995) *J. Invest. Dermatol.* 104:251–255.
Blakely et al. (1991) *Anal. Biochem.* 194:302–308.
Bligh et al. (1959) *Can. J. Biochem. Physiol.* 37:911–917.
Boyington et al. (1993) *Science* 260:1482–1486.
Brash et al. (1990) *Method. Enzymol.* 187:187–192.
Brash et al. (1996) *J. Biol. Chem.* 271:20549–20557.
Brash et al. (1996) *J. Biol. Chem.* 271:20949–20957.
Bryant et al. (1982) *J. Biol. Chem.* 257:6050–6055.
Capdevila et al. (1986) *Biochem. Biophys. Res. Commun.* 141:1007–1011.
Chen et al. (1994) *J. Biol. Chem.* 269:13979–13987.
Chen et al. (1994) *Nature* 372:179–182.
Chen et al. (1995) *J. Biol. Chem.* 270:17993–17999.
Crea et al., (1978) *Proc. Natl. Acad. Sci. U.S.A,* 75:5765.
Dixon et al. (1988) *Proc. Natl. Acad. Sci. USA* 85:416–420.
Eichenlaub, R. *J. Bacteriol* 138:559–566, 1979.
Fischer et al. (1987) *Carcinogenesis* 8:421–424.
Fischer et al. (1987) *Cancer Res.* 47:3174–3179.
Fischer et al. (1988) *Cancer Res.* 48:658–664.
Funk et al. (1990) *Proc. Natl. Acad. Sci. USA* 87:5638–5642.
Funk et al. (1993) *Prog. Nuc. Acid Res. Mol. Biol.* 45:67–98.
Funk et al. (1996) *J. Biol. Chem.* 271:23338–23344.
Furstenberger et al. (1991) *J. Biol. Chem.* 266:15738–15745.
Gschwendt et al. (1986) *Carcinogenesis* 7:449–455.
Hada et al. (1991) *Biochim. Biophys. Acta* 1083:89–93.
Hamberg et al. (1980) *Biochim. Biophys. Acta* 617:545–547.
Hammarstrbm et al. (1975) *Proc. Natl. Acad. Sci. USA* 72:5130–5134.
Henneicke-von Zepelin et al. (1991) *J. Invest. Derrmatol.* 97:291–297.
Holtzman et al. (1989) *J. Clin. Invest.* 84:1446–1453.
Hopp, U.S. Pat. No. 4,554,101.
Howell et al. *Antibodies A Laboratory Manual,* Cold Spring Harbor Laboratory, 1988.
Hughes et al. (1991) *Biochim. Biophys. Acta* 1081:347–354.
Hussain et al. (1994) *Amer. J. Physiol.* 266:C243–C253.
Ingram et al. (1988) *Lipids* 23:340–344.
Izumi et al. (1990) *Proc. Natl. Acad. Sci. USA* 87:7477–7481.
Kyte, J., and R. F. Doolittle (1982) *J. Mol. Biol.* 157: 105.
Lehmann et al. (1992) *Anal. Biochem.* 204:158–170 Liminga et al. (1994) *Exp. Eye Res.* 59:313–321.
Liminga et al. (1994) *Biochim. Biophys. Acta* 1210:288–296.
Matsumoto et al. (1988) *Proc. Natl. Acad. Sci. USA* 85:26–30.
Messing et al., *Third Cleveland Symposium on Macromolecules and Recombinant DNA,* Editor A. Walton, Elsevier, Amsterdam (1981).
Minor et al. (1996) *Biochemistry* 35:10687–10701.
Murray et al. (1988) *Arch. Biochem. Biophys.* 265:514–523.
Nadel et al. (1991) *J. Clin. Invest.* 87:1139–1145.
Nugteren et al. (1975) *Biochim. Bikophys. Acta* 380:299–307.
Nugteren et al. (1987) *Biochim. Biophys. Acta* 921:135–141
Oesterling et al. (1996) *Prostate* 6:67–73.
Oliw et al. (1989) *Biochim. Biophys. Acta* 1002:283–291.
Oliw et al. (1993) *J. Reprod. Fertil.* 99:195–199.
Sambrook, C. et al. (1989) *Molecular Cloning: A Laboratory Manual* (Cold Spring Harbor Laboratory Press, Cold Spring Harbor, N.Y.).
Schewe et al. (1975) *FEBS Lett.* 60:149–153.
Shannon et al. (1991) *Am. J. Physiol.* 261:L399–405.
Shannon et al. (1993) *Am. Rev. Respir. Dis.* 147:1024–1028.
Sigal et al. (1988) *Biochem. Biophys. Res. Comm.* 157: 457–464.
Sigal et al. (1992) *Am. J. Physiol.* 262:L392–398.
Soberman et al. (1985) *J. Biol. Chem.* 260:4508–4515.

Sun et al. (1996) *J. Biol. Chem.* 271, 24055–24062.
Takahashi et al. (1993) *J. Biol. Chem.* 268:16443–16448.
U.S. Pat. No. 4,196,265
U.S. Pat. No. 4,683,202
van Dijk et al. (1995) *Biochim. Biophys. Acta* 1259:4–8.
Wetmur & Davidson, *J. Mol. Biol.* 31:349–370, 1968.

Woollard et al. (1986) *Biochem. Biophys. Res. Commun.* 136(1):169–175.
Yoshimoto et al. (1990) *Biochem. Biophys. Res. Comm.* 172: 1230–1235.
Yu et al. (1995) *J. Biol. Chem.* 270:23975–23983.
Ziboh et al. (1988) *Prog. Lipid Res.* 27:81–105.

---

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
      (A) LENGTH: 2685 base pairs
      (B) TYPE: nucleic acid
      (C) STRANDEDNESS: double
      (D) TOPOLOGY: unknown (xi) SEQUENCE DESCRIPTION: SEQ ID NO: 1:

```
CAGGCGTGTC CCAGGGGGAG CCCCGCTCTG CAGCCCTGTG CGCCGTAGAG AGCTGGACTT           60

AGGCTGGCAG C ATG GCC GAG TTC AGG GTC AGG GTG TCC ACC GGA GAA GCC          110
             Met Ala Glu Phe Arg Val Arg Val Ser Thr Gly Glu Ala
               1               5                  10

TTC GGG GCT GGC ACA TGG GAC AAA GTG TCT GTC AGC ATC GTG GGG ACC           158
Phe Gly Ala Gly Thr Trp Asp Lys Val Ser Val Ser Ile Val Gly Thr
 15              20                  25

CGG GGA GAG AGC CCC CCA CTG CCC CTG GAC AAT CTC GGC AAG GAG TTC           206
Arg Gly Glu Ser Pro Pro Leu Pro Leu Asp Asn Leu Gly Lys Glu Phe
 30              35                  40                  45

ACT GCG GGC GCT GAG GAG GAC TTC CAG GTG ACG CTC CCG GAG GAC GTA           254
Thr Ala Gly Ala Glu Glu Asp Phe Gln Val Thr Leu Pro Glu Asp Val
                 50                  55                  60

GGC CGA GTG CTG CTG CTG CGC GTG CAC AAG GCG CCC CCA GTG CTG CCC           302
Gly Arg Val Leu Leu Leu Arg Val His Lys Ala Pro Pro Val Leu Pro
                 65                  70                  75

CTG CTG GGG CCC CTG GCC CCG GAT GCC TGG TTC TGC CGC TGG TTC CAG           350
Leu Leu Gly Pro Leu Ala Pro Asp Ala Trp Phe Cys Arg Trp Phe Gln
             80                  85                  90

CTG ACA CCG CCG CGG GGC GGC CAC CTC CTC TTC CCC TGC TAC CAG TGG           398
Leu Thr Pro Pro Arg Gly Gly His Leu Leu Phe Pro Cys Tyr Gln Trp
 95                 100                 105

CTG GAG GGG GCG GGG ACC CTG GTG CTG CAG GAG GGT ACA GCC AAG GTG           446
Leu Glu Gly Ala Gly Thr Leu Val Leu Gln Glu Gly Thr Ala Lys Val
110                 115                 120                 125

TCC TGG GCA GAC CAC CAC CCT GTG CTC CAG CAA CAG CGC CAG GAG GAG           494
Ser Trp Ala Asp His His Pro Val Leu Gln Gln Gln Arg Gln Glu Glu
                130                 135                 140

CTT CAG GCC CGG CAG GAG ATG TAC CAG TGG AAG GCT TAC AAC CCA GGT           542
Leu Gln Ala Arg Gln Glu Met Tyr Gln Trp Lys Ala Tyr Asn Pro Gly
                145                 150                 155

TGG CCT CAC TGC CTG GAT GAA AAG ACA GTG GAA GAC TTG GAG CTC AAT           590
Trp Pro His Cys Leu Asp Glu Lys Thr Val Glu Asp Leu Glu Leu Asn
            160                 165                 170

ATC AAA TAC TCC ACA GCC AAG AAT GCC AAC TTT TAT CTA CAA GCT GGC           638
Ile Lys Tyr Ser Thr Ala Lys Asn Ala Asn Phe Tyr Leu Gln Ala Gly
175                 180                 185

TCT GCT TTT GCA GAG ATG AAA ATC AAG GGG TTG CTG GAC CGC AAG GGG           686
```

-continued

```
Ser Ala Phe Ala Glu Met Lys Ile Lys Gly Leu Leu Asp Arg Lys Gly
190                 195                 200                 205

CTC TGG AGG AGT CTG AAT GAG ATG AAA AGG ATC TTC AAC TTC CGG AGG        734
Leu Trp Arg Ser Leu Asn Glu Met Lys Arg Ile Phe Asn Phe Arg Arg
            210                 215                 220

ACC CCA GCA GCT GAG CAC GCA TTT GAG CAC TGG CAG GAG GAT GCC TTC        782
Thr Pro Ala Ala Glu His Ala Phe Glu His Trp Gln Glu Asp Ala Phe
                225                 230                 235

TTC GCC TCC CAG TTC CTG AAT GGT CTC AAC CCT GTC CTG ATC CGC CGC        830
Phe Ala Ser Gln Phe Leu Asn Gly Leu Asn Pro Val Leu Ile Arg Arg
            240                 245                 250

TGT CAC TAC CTC CCA AAG AAC TTC CCC GTC ACT GAT GCC ATG GTG GCC        878
Cys His Tyr Leu Pro Lys Asn Phe Pro Val Thr Asp Ala Met Val Ala
        255                 260                 265

TCA TTG TTG GGT CCT GGG ACC AGC TTG CAG GCT GAG CTA GAG AAG GGC        926
Ser Leu Leu Gly Pro Gly Thr Ser Leu Gln Ala Glu Leu Glu Lys Gly
270                 275                 280                 285

TCC CTG TTC TTG GTG GAT CAC GGC ATC CTC TCT GGC ATC CAG ACC AAT        974
Ser Leu Phe Leu Val Asp His Gly Ile Leu Ser Gly Ile Gln Thr Asn
            290                 295                 300

GTC ATT AAT GGG AAG CCG CAG TTC TCT GCG GCC CCA ATG ACC CTG CTA       1022
Val Ile Asn Gly Lys Pro Gln Phe Ser Ala Ala Pro Met Thr Leu Leu
        305                 310                 315

TAC CAG AGC CCA GGC TGC GGG CCG CTG CTG CCT CTC GCC ATC CAG CTC       1070
Tyr Gln Ser Pro Gly Cys Gly Pro Leu Leu Pro Leu Ala Ile Gln Leu
        320                 325                 330

AGC CAG ACC CCC GGC CCA AAC AGC CCC ATC TTC CTG CCC ACT GAT GAC       1118
Ser Gln Thr Pro Gly Pro Asn Ser Pro Ile Phe Leu Pro Thr Asp Asp
    335                 340                 345

AAG TGG GAC TGG TTG CTG GCC AAG ACC TGG GTG CGC AAT GCC GAG TTC       1166
Lys Trp Asp Trp Leu Leu Ala Lys Thr Trp Val Arg Asn Ala Glu Phe
350                 355                 360                 365

TCC TTC CAT GAG GCC CTC ACG CAC CTG CTG CAC TCA CAT CTG CTG CCT       1214
Ser Phe His Glu Ala Leu Thr His Leu Leu His Ser His Leu Leu Pro
            370                 375                 380

GAG GTC TTC ACC CTG GCT ACC CTG CGT CAG CTG CCC CAC TGC CAC CCT       1262
Glu Val Phe Thr Leu Ala Thr Leu Arg Gln Leu Pro His Cys His Pro
        385                 390                 395

CTC TTC AAG CTG CTG ATC CCG CAC ACC CGA TAC ACC CTG CAC ATC AAC       1310
Leu Phe Lys Leu Leu Ile Pro His Thr Arg Tyr Thr Leu His Ile Asn
        400                 405                 410

ACA CTC GCC CGG GAG CTG CTT ATC GTG CCA GGG CAG GTG GTG GAC AGG       1358
Thr Leu Ala Arg Glu Leu Leu Ile Val Pro Gly Gln Val Val Asp Arg
    415                 420                 425

TCC ACA GGC ATC GGC ATT GAA GGC TTC TCT GAG TTG ATA CAG AGG AAC       1406
Ser Thr Gly Ile Gly Ile Glu Gly Phe Ser Glu Leu Ile Gln Arg Asn
430                 435                 440                 445

ATG AAG CAG CTG AAC TAT TCT CTC CTG TGT CTG CCT GAG GAT ATC CGG       1454
Met Lys Gln Leu Asn Tyr Ser Leu Leu Cys Leu Pro Glu Asp Ile Arg
            450                 455                 460

ACC CGA GGA GTT GAA GAC ATC CCA GGC TAC TAC TAC CGT GAT GAT GGG       1502
Thr Arg Gly Val Glu Asp Ile Pro Gly Tyr Tyr Tyr Arg Asp Asp Gly
        465                 470                 475

ATG CAG ATT TGG GGT GCA GTG GAA CGC TTT GTC TCT GAA ATC ATC GGT       1550
Met Gln Ile Trp Gly Ala Val Glu Arg Phe Val Ser Glu Ile Ile Gly
        480                 485                 490

ATC TAC TAC CCA AGT GAT GAG TCT GTC CAA GAT GAC AGA GAG CTC CAG       1598
Ile Tyr Tyr Pro Ser Asp Glu Ser Val Gln Asp Asp Arg Glu Leu Gln
495                 500                 505
```

```
GCC TGG GTC AGA GAG ATC TTC TCC AAG GGC TTC CTA AAC CAG GAG AGC    1646
Ala Trp Val Arg Glu Ile Phe Ser Lys Gly Phe Leu Asn Gln Glu Ser
510                 515                 520                 525

TCA GGT ATC CCT TCC TCA CTG GAG ACC CGG GAA GCC CTG GTG CAG TAT    1694
Ser Gly Ile Pro Ser Ser Leu Glu Thr Arg Glu Ala Leu Val Gln Tyr
                530                 535                 540

GTC ACC ATG GTG ATA TTC ACC TGC TCA GCC AAG CAT GCG GCT GTC AGT    1742
Val Thr Met Val Ile Phe Thr Cys Ser Ala Lys His Ala Ala Val Ser
            545                 550                 555

GCA GGG CAG TTT GAC TCC TGT GCT TGG ATG CCC AAC CTG CCA CCC AGC    1790
Ala Gly Gln Phe Asp Ser Cys Ala Trp Met Pro Asn Leu Pro Pro Ser
        560                 565                 570

ATG CAG CTG CCA CCA CCC ACC TCC AAA GGC CTG GCA ACA TGC GAG GGC    1838
Met Gln Leu Pro Pro Pro Thr Ser Lys Gly Leu Ala Thr Cys Glu Gly
575                 580                 585

TTC ATA GCC ACC CTC CCA CCT GTC AAT GCC ACA TGT GAT GTC ATC CTT    1886
Phe Ile Ala Thr Leu Pro Pro Val Asn Ala Thr Cys Asp Val Ile Leu
590                 595                 600                 605

GCT CTC TGG TTG CTG AGC AAG GAG CCT GGA GAC CAA AGG CCC CTG GGC    1934
Ala Leu Trp Leu Leu Ser Lys Glu Pro Gly Asp Gln Arg Pro Leu Gly
                610                 615                 620

ACC TAT CCG GAT GAG CAC TTC ACA GAG GAG GCC CCT CGG CGG AGC ATC    1982
Thr Tyr Pro Asp Glu His Phe Thr Glu Glu Ala Pro Arg Arg Ser Ile
            625                 630                 635

GCC ACC TTC CAG AGC CGC CTG GCC CAG ATC TCG AGG GGC ATC CAG GAG    2030
Ala Thr Phe Gln Ser Arg Leu Ala Gln Ile Ser Arg Gly Ile Gln Glu
        640                 645                 650

CGG AAC CGG GGC CTG GTG CTG CCC TAC ACC TAC CTA GAC CCT CCC CTC    2078
Arg Asn Arg Gly Leu Val Leu Pro Tyr Thr Tyr Leu Asp Pro Pro Leu
655                 660                 665

ATC GAG AAC AGC GTC TCC ATC TAAATCCCAG GGAACACAG GCCCAGATGA        2129
Ile Glu Asn Ser Val Ser Ile
670                 675

CATCCCTTTG ACCACATCGC TCTAGGATAA CTGGCACCCA GAGAAAAGGA CTCCTCAGAA  2189

AAAACAGGCC CCCATGTGCC TCTCCTGGGA CAACCAGACT CTGTAACTCA CCCCCACCAC  2249

CATACACACA CACAAAAACA GAAACAAAAT CAAAACAGAG AAAGCAGAAA ATCTACCAAG  2309

AACAGAGTCT CAGGACAGAA CCACTGAGTC TTTTGGAGGC TCCAAGCCTC AAAGTGCCCG  2369

CAGAGCCCAC CTTGAGGGTT TTGCTAGTTG GTTTTGTTTT GCGTTTACAG CCGTGGGGGG  2429

AAGCACATAA TCCCGCCCCA GGGCCCACTA GCATCCACTG ATTGGACCTT ATGGTCACCC  2489

AACTCAAGGA CAGCCACCAA GAAGTGGCTG CCAAAGAGAC TGGGCGCAGT GGCTCATGCC  2549

CATAATCCCA GCACTTTGGG AGATGGAGGC GGGAAAATCA TTTGAGGTCA GAAGTTCAAG  2609

GCCAGCCTGG ACGACATAGC GAGACTCCAC CTCTACCAAA AATAAAAAT TAAAAACAA    2669

AAAAAAAAAA AAAAA                                                   2685

(2) INFORMATION FOR SEQ ID NO: 2:

(i) SEQUENCE CHARACTERISTICS:
        (A) LENGTH: 676 amino acids
        (B) TYPE: amino acid
        (C) STRANDEDNESS: single
        (D) TOPOLOGY: unknown (xi) SEQUENCE DESCRIPTION: SEQ ID NO: 2:

Met Ala Glu Phe Arg Val Arg Val Ser Thr Gly Glu Ala Phe Gly Ala
1               5                   10                  15

Gly Thr Trp Asp Lys Val Ser Val Ser Ile Val Gly Thr Arg Gly Glu
```

-continued

```
            20                  25                  30
Ser Pro Pro Leu Pro Leu Asp Asn Leu Gly Lys Glu Phe Thr Ala Gly
            35                  40                  45
Ala Glu Glu Asp Phe Gln Val Thr Leu Pro Glu Asp Val Gly Arg Val
 50                  55                  60
Leu Leu Leu Arg Val His Lys Ala Pro Pro Val Leu Pro Leu Leu Gly
 65                  70                  75                  80
Pro Leu Ala Pro Asp Ala Trp Phe Cys Arg Trp Phe Gln Leu Thr Pro
                     85                  90                  95
Pro Arg Gly Gly His Leu Leu Phe Pro Cys Tyr Gln Trp Leu Glu Gly
                    100                 105                 110
Ala Gly Thr Leu Val Leu Gln Glu Gly Thr Ala Lys Val Ser Trp Ala
            115                 120                 125
Asp His His Pro Val Leu Gln Gln Arg Gln Glu Glu Leu Gln Ala
            130                 135                 140
Arg Gln Glu Met Tyr Gln Trp Lys Ala Tyr Asn Pro Gly Trp Pro His
145                 150                 155                 160
Cys Leu Asp Glu Lys Thr Val Glu Asp Leu Glu Leu Asn Ile Lys Tyr
                    165                 170                 175
Ser Thr Ala Lys Asn Ala Asn Phe Tyr Leu Gln Ala Gly Ser Ala Phe
                    180                 185                 190
Ala Glu Met Lys Ile Lys Gly Leu Leu Asp Arg Lys Gly Leu Trp Arg
            195                 200                 205
Ser Leu Asn Glu Met Lys Arg Ile Phe Asn Phe Arg Arg Thr Pro Ala
            210                 215                 220
Ala Glu His Ala Phe Glu His Trp Gln Glu Asp Ala Phe Phe Ala Ser
225                 230                 235                 240
Gln Phe Leu Asn Gly Leu Asn Pro Val Leu Ile Arg Arg Cys His Tyr
                    245                 250                 255
Leu Pro Lys Asn Phe Pro Val Thr Asp Ala Met Val Ala Ser Leu Leu
                    260                 265                 270
Gly Pro Gly Thr Ser Leu Gln Ala Glu Leu Glu Lys Gly Ser Leu Phe
                    275                 280                 285
Leu Val Asp His Gly Ile Leu Ser Gly Ile Gln Thr Asn Val Ile Asn
            290                 295                 300
Gly Lys Pro Gln Phe Ser Ala Ala Pro Met Thr Leu Leu Tyr Gln Ser
305                 310                 315                 320
Pro Gly Cys Gly Pro Leu Leu Pro Leu Ala Ile Gln Leu Ser Gln Thr
                    325                 330                 335
Pro Gly Pro Asn Ser Pro Ile Phe Leu Pro Thr Asp Asp Lys Trp Asp
                    340                 345                 350
Trp Leu Leu Ala Lys Thr Trp Val Arg Asn Ala Glu Phe Ser Phe His
            355                 360                 365
Glu Ala Leu Thr His Leu Leu His Ser His Leu Leu Pro Glu Val Phe
            370                 375                 380
Thr Leu Ala Thr Leu Arg Gln Leu Pro His Cys His Pro Leu Phe Lys
385                 390                 395                 400
Leu Leu Ile Pro His Thr Arg Tyr Thr Leu His Ile Asn Thr Leu Ala
                    405                 410                 415
Arg Glu Leu Leu Ile Val Pro Gly Gln Val Val Asp Arg Ser Thr Gly
            420                 425                 430
Ile Gly Ile Glu Gly Phe Ser Glu Leu Ile Gln Arg Asn Met Lys Gln
            435                 440                 445
```

```
Leu Asn Tyr Ser Leu Leu Cys Leu Pro Glu Asp Ile Arg Thr Arg Gly
        450                 455                 460

Val Glu Asp Ile Pro Gly Tyr Tyr Arg Asp Asp Gly Met Gln Ile
465                 470                 475                 480

Trp Gly Ala Val Glu Arg Phe Val Ser Glu Ile Ile Gly Ile Tyr Tyr
                485                 490                 495

Pro Ser Asp Glu Ser Val Gln Asp Arg Glu Leu Gln Ala Trp Val
            500                 505                 510

Arg Glu Ile Phe Ser Lys Gly Phe Leu Asn Gln Glu Ser Ser Gly Ile
        515                 520                 525

Pro Ser Ser Leu Glu Thr Arg Glu Ala Leu Val Gln Tyr Val Thr Met
        530                 535                 540

Val Ile Phe Thr Cys Ser Ala Lys His Ala Ala Val Ser Ala Gly Gln
545                 550                 555                 560

Phe Asp Ser Cys Ala Trp Met Pro Asn Leu Pro Pro Ser Met Gln Leu
                565                 570                 575

Pro Pro Pro Thr Ser Lys Gly Leu Ala Thr Cys Glu Gly Phe Ile Ala
            580                 585                 590

Thr Leu Pro Pro Val Asn Ala Thr Cys Asp Val Ile Leu Ala Leu Trp
        595                 600                 605

Leu Leu Ser Lys Glu Pro Gly Asp Gln Arg Pro Leu Gly Thr Tyr Pro
610                 615                 620

Asp Glu His Phe Thr Glu Glu Ala Pro Arg Arg Ser Ile Ala Thr Phe
625                 630                 635                 640

Gln Ser Arg Leu Ala Gln Ile Ser Arg Gly Ile Gln Glu Arg Asn Arg
                645                 650                 655

Gly Leu Val Leu Pro Tyr Thr Tyr Leu Asp Pro Pro Leu Ile Glu Asn
            660                 665                 670

Ser Val Ser Ile
        675

(2) INFORMATION FOR SEQ ID NO: 3:

(i) SEQUENCE CHARACTERISTICS:
        (A) LENGTH: 3205 base pairs
        (B) TYPE: nucleic acid
        (C) STRANDEDNESS: double
        (D) TOPOLOGY: unknown (xi) SEQUENCE DESCRIPTION: SEQ ID NO: 3:

ATG GCG AAA TGC AGG GTG AGA GTA TCC ACG GGG GAA GCC TGT GGG GCT        48
Met Ala Lys Cys Arg Val Arg Val Ser Thr Gly Glu Ala Cys Gly Ala
1               5                   10                  15

GGC ACA TGG GAC AAA GTG TCT GTC AGC ATC GTG GGA ACC CAC GGA GAG        96
Gly Thr Trp Asp Lys Val Ser Val Ser Ile Val Gly Thr His Gly Glu
                20                  25                  30

AGC CCC TTA GTA CCT CTG GAC CAT CTG GGC AAG GAG TTC AGC GCC GGT       144
Ser Pro Leu Val Pro Leu Asp His Leu Gly Lys Glu Phe Ser Ala Gly
            35                  40                  45

GCT GAA GAA GAC TTC GAG GTG ACG CTT CCC CAG GAC GTA GGC ACT GTG       192
Ala Glu Glu Asp Phe Glu Val Thr Leu Pro Gln Asp Val Gly Thr Val
        50                  55                  60

CTG ATG CTG CGA GTC CAC AAA GCA CCC CCG GAA GTG TCC CTC CCG CTT       240
Leu Met Leu Arg Val His Lys Ala Pro Pro Glu Val Ser Leu Pro Leu
65                  70                  75                  80

ATG TCT TTC CGT TCT GAT GCC TGG TTC TGC CGC TGG TTC GAG CTG GAG       288
Met Ser Phe Arg Ser Asp Ala Trp Phe Cys Arg Trp Phe Glu Leu Glu
```

```
             85                  90                  95
TGG CTA CCT GGG GCT GCA CTC CAC TTC CCC TGT TAT CAG TGG CTG GAA     336
Trp Leu Pro Gly Ala Ala Leu His Phe Pro Cys Tyr Gln Trp Leu Glu
            100                 105                 110

GGG GCG GGG GAG CTG GTG CTG AGA GAG GGA GCA GCA AAG GTG TCC TGG     384
Gly Ala Gly Glu Leu Val Leu Arg Glu Gly Ala Ala Lys Val Ser Trp
        115                 120                 125

CAA GAC CAT CAC CCT ACA CTG CAG GAT CAG CGC CAG AAG GAG CTT GAG     432
Gln Asp His His Pro Thr Leu Gln Asp Gln Arg Gln Lys Glu Leu Glu
    130                 135                 140

TCC AGG CAG AAG ATG TAC AGC TGG AAG ACT TAC ATT GAA GGT TGG CCT     480
Ser Arg Gln Lys Met Tyr Ser Trp Lys Thr Tyr Ile Glu Gly Trp Pro
145                 150                 155                 160

CGC TGC CTT GAC CAC GAG ACT GTG AAA GAC TTG GAC CTC AAC ATC AAG     528
Arg Cys Leu Asp His Glu Thr Val Lys Asp Leu Asp Leu Asn Ile Lys
                165                 170                 175

TAC TCT GCG ATG AAG AAT GCC AAA CTC TTC TTT AAA GCC CAC TCC GCG     576
Tyr Ser Ala Met Lys Asn Ala Lys Leu Phe Phe Lys Ala His Ser Ala
            180                 185                 190

TAT ACG GAG CTG AAA GTC AAA GGG CTC CTG GAC CGC ACA GGA CTC TGG     624
Tyr Thr Glu Leu Lys Val Lys Gly Leu Leu Asp Arg Thr Gly Leu Trp
        195                 200                 205

AGG AGT CTG AGG GAG ATG AGA AGG CTG TTT AAC TTC CGC AAG ACT CCA     672
Arg Ser Leu Arg Glu Met Arg Arg Leu Phe Asn Phe Arg Lys Thr Pro
    210                 215                 220

GCA GCA GAG TAT GTG TTT GCA CAC TGG CAG GAA GAT GCC TTC TTC GCC     720
Ala Ala Glu Tyr Val Phe Ala His Trp Gln Glu Asp Ala Phe Phe Ala
225                 230                 235                 240

TCC CAG TTC CTA AAT GGC ATC AAC CCG GTC CTG ATT CGC CGC TGT CAC     768
Ser Gln Phe Leu Asn Gly Ile Asn Pro Val Leu Ile Arg Arg Cys His
                245                 250                 255

AGT CTC CCA AAC AAC TTC CCG GTC ACT GAT GAA ATG GTG GCC CCA GTG     816
Ser Leu Pro Asn Asn Phe Pro Val Thr Asp Glu Met Val Ala Pro Val
            260                 265                 270

CTG GGC CCT GGA ACC AGT CTG CAG GCT GAG TTG GAG AAG GGC TCC CTG     864
Leu Gly Pro Gly Thr Ser Leu Gln Ala Glu Leu Glu Lys Gly Ser Leu
        275                 280                 285

TTC TTG GTG GAT CAT GGC ATT CTT TCT GGA GTC CAC ACC AAC ATC CTC     912
Phe Leu Val Asp His Gly Ile Leu Ser Gly Val His Thr Asn Ile Leu
    290                 295                 300

AAT GGA AAG CCT CAG TTC TCT GCA GCC CCG ATG ACC CTG TTA CAC CAG     960
Asn Gly Lys Pro Gln Phe Ser Ala Ala Pro Met Thr Leu Leu His Gln
305                 310                 315                 320

AGC TCA GGG TCC GGA CCC CTG CTT CCC ATT GCC ATC CAG CTC AAA CAG    1008
Ser Ser Gly Ser Gly Pro Leu Leu Pro Ile Ala Ile Gln Leu Lys Gln
                325                 330                 335

ACT CCC GGG CCA GAC AAC CCC ATC TTC CTG CCC AGC GAT GAC ACG TGG    1056
Thr Pro Gly Pro Asp Asn Pro Ile Phe Leu Pro Ser Asp Asp Thr Trp
            340                 345                 350

GAC TGG TTG CTG GCC AAG ACC TGG GTT CGC AAT TCT GAG TTT TAC ATC    1104
Asp Trp Leu Leu Ala Lys Thr Trp Val Arg Asn Ser Glu Phe Tyr Ile
        355                 360                 365

CAT GAG GCT GTC ACA CAT CTG CTG CAT GCC CAT CTG ATT CCA GAA GTC    1152
His Glu Ala Val Thr His Leu Leu His Ala His Leu Ile Pro Glu Val
    370                 375                 380

TTT GCC TTG GCC ACA TTA CGT CAG CTG CCT AGG TGT CAC CCT CTC TTC    1200
Phe Ala Leu Ala Thr Leu Arg Gln Leu Pro Arg Cys His Pro Leu Phe
385                 390                 395                 400

AAG CTA TTG ATT CCT CAC ATT CGG TAC ACA CTG CAC ATC AAC ACG CTT    1248
```

```
                Lys Leu Leu Ile Pro His Ile Arg Tyr Thr Leu His Ile Asn Thr Leu
                                405                 410                 415
GCC CGG GAG CTG CTC GTT GCC CCT GGG AAG TTG ATA GAC AAG TCC ACA          1296
Ala Arg Glu Leu Leu Val Ala Pro Gly Lys Leu Ile Asp Lys Ser Thr
            420                 425                 430

GGC CTT GGC ACT GGG GGA TTC TCT GAC CTG ATA AAG AGA AAC ATG GAG          1344
Gly Leu Gly Thr Gly Gly Phe Ser Asp Leu Ile Lys Arg Asn Met Glu
            435                 440                 445

CAG CTG AAC TAC TCT GTC CTG TGT CTC CCT GAA GAT ATC CGA GCC CGA          1392
Gln Leu Asn Tyr Ser Val Leu Cys Leu Pro Glu Asp Ile Arg Ala Arg
        450                 455                 460

GGT GTG GAA GAC ATC CCA GGC TAC TAT TAC CGA GAT GAT GGG ATG CAG          1440
Gly Val Glu Asp Ile Pro Gly Tyr Tyr Tyr Arg Asp Asp Gly Met Gln
465                 470                 475                 480

ATC TGG GGG GCA ATA AAG AGC TTT GTC TCT GAA ATA GTC AGC ATC TAC          1488
Ile Trp Gly Ala Ile Lys Ser Phe Val Ser Glu Ile Val Ser Ile Tyr
                485                 490                 495

TAT CCA AGT GAC ACA TCC GTC CAA GAT GAC CAA GAG CTC CAG GCC TGG          1536
Tyr Pro Ser Asp Thr Ser Val Gln Asp Asp Gln Glu Leu Gln Ala Trp
            500                 505                 510

GTG AGG GAG ATC TTC TCT GAG GGC TTC CTC GGC CGA GAA AGC TCA GGT          1584
Val Arg Glu Ile Phe Ser Glu Gly Phe Leu Gly Arg Glu Ser Ser Gly
            515                 520                 525

ATG CCC TCC TTG TTG GAT ACC CGG GAA GCC CTG GTC CAG TAT ATC ACC          1632
Met Pro Ser Leu Leu Asp Thr Arg Glu Ala Leu Val Gln Tyr Ile Thr
        530                 535                 540

ATG GTG ATA TTC ACC TGC TCA GCC AAG CAT GCA GCT GTC AGT TCA GGC          1680
Met Val Ile Phe Thr Cys Ser Ala Lys His Ala Ala Val Ser Ser Gly
545                 550                 555                 560

CAG TTC GAC TCT TGT GTT TGG ATG CCC AAT CTG CCA CCT ACC ATG CAG          1728
Gln Phe Asp Ser Cys Val Trp Met Pro Asn Leu Pro Pro Thr Met Gln
                565                 570                 575

CTA CCA CCA CCT ACT TCC AAA GGC CAG GCC CGG CCT GAG AGT TTC ATA          1776
Leu Pro Pro Pro Thr Ser Lys Gly Gln Ala Arg Pro Glu Ser Phe Ile
            580                 585                 590

GCC ACG CTC CCA GCA GTT AAT TCG TCA AGT TAT CAC ATC ATT GCT CTC          1824
Ala Thr Leu Pro Ala Val Asn Ser Ser Ser Tyr His Ile Ile Ala Leu
            595                 600                 605

TGG CTG CTA AGC GCA GAA CCT GGG GAC CAA AGG CCC CTG GGC CAC TAT          1872
Trp Leu Leu Ser Ala Glu Pro Gly Asp Gln Arg Pro Leu Gly His Tyr
        610                 615                 620

CCA GAT GAA CAC TTC ACA GAG GAT GCC CCC CGG CGA AGC GTG GCT GCC          1920
Pro Asp Glu His Phe Thr Glu Asp Ala Pro Arg Arg Ser Val Ala Ala
625                 630                 635                 640

TTC CAG AGA AAG CTG ATC CAG ATC TCC AAG GGC ATC AGG GAG AGG AAC          1968
Phe Gln Arg Lys Leu Ile Gln Ile Ser Lys Gly Ile Arg Glu Arg Asn
                645                 650                 655

CGA GGC CTG GCA CTG CCC TAC ACC TAC CTG GAT CCT CCC CTC ATT GAG          2016
Arg Gly Leu Ala Leu Pro Tyr Thr Tyr Leu Asp Pro Pro Leu Ile Glu
            660                 665                 670

AAC AGT GTC TCC ATC TAACATCTTG GAGAAGACAG TCCTGTGTGA CATATAGAAC          2071
Asn Ser Val Ser Ile
            675

TCTTGACCAT GCCTCTCCAG GCTAAGTCCC CGTATGCTTC TCCTGGACAA CCAAGCCCCA       2131

TCTTACACAC ACACACACAC ACACACACCT AATAAAATCG AAACAGAAAA ACCTAAACTC       2191

CCACAGAAGG CAAGATCTCA CACAGCAGAG AGCCATCCAA ATGTTTGGAG ACCCTGAGCT       2251

TCAGCTCTGA TTAACGGCTT TGCTGGTTTG CTTTGCTTTC TATTCCATTA ACCATGGACG       2311
```

-continued

```
GTAACAGAAA GCACAGAACC CTGGTTCACT GCACAAAGCC ACTGAGATCT CACCCTCACC    2371

TGACACAAAG GCAGCTATCA TACAGGCTTA TCAGGAACAC AGGAATTTGT CCAATCAAAG    2431

CCTACCCACT AGGTCCATCG TGACCTACGA CCTCACACTG GCATGCTTTA GCTTTGAGAA    2491

GGGATTACTG GAGTCAGGTA CGAAGAGAAG GACAGGACGA AGGCATGGCT CCATGTGGAA    2551

GAACATATCT GCTCTTCCAG ATGACCAGGG TAGCTCACAG CCATGTGTCA TTCTAACTCC    2611

AGAGGTCTCT AGTGGCCATG AAGACTCCAG GCATTCAGGG GATATACCAG TAGACACCAA    2671

AATTATACTT TTTAAGAGAG AGGATGGGCT GGAGAGATGG CTCAGCGGTT AAGAGCACTG    2731

ACTGCTCTTC CAGAGATCCT GAGTTCAATT CCCAGCAACC ACATGGTGGC TCACAACCAT    2791

CTGTAATGGG ATTCGATGCC CTCTTCTGGC GTGTCTGAAG ACAGCGACAG TGTATGCACA    2851

TATATAAAAT AAATAAATCT TTAAAAAACA AAACAAGAGA GAGGGACATG CTACCATTTC    2911

TACCTCACTT CTTCTCAAAG CCACCCCTAA AGTGAATTGT GAACCAGGTC CCCTTTGCAG    2971

AGAGTTAGAA GATATTCTCA AACCTCTAAT ACCTTCACAT CTAAAATCCA TCTTCATTCC    3031

AAAATTCCAA TATTTTATAT ACACTCTCCA GTTTGGTGGG TGAGGGGTTG TTTTTTGTTT    3091

GGTTTGGTTT GGTTGGGGTT TTGTTTTTGT TTTTGATTTT GTTTTTCTCT GGTTCAGACT    3151

CCATGGACGT TCATTAATGT CATAAATGAG TTCATTCCAA AAAAAAAAAA AAAA          3205
```

(2) INFORMATION FOR SEQ ID NO: 4:

(i) SEQUENCE CHARACTERISTICS:
        (A) LENGTH: 677 amino acids
        (B) TYPE: amino acid
        (C) STRANDEDNESS: single
        (D) TOPOLOGY: unknown (xi) SEQUENCE DESCRIPTION: SEQ ID NO: 4:

```
Met Ala Lys Cys Arg Val Arg Val Ser Thr Gly Glu Ala Cys Gly Ala
 1               5                  10                  15

Gly Thr Trp Asp Lys Val Ser Val Ser Ile Val Gly Thr His Gly Glu
                20                  25                  30

Ser Pro Leu Val Pro Leu Asp His Leu Gly Lys Glu Phe Ser Ala Gly
            35                  40                  45

Ala Glu Glu Asp Phe Glu Val Thr Leu Pro Gln Asp Val Gly Thr Val
        50                  55                  60

Leu Met Leu Arg Val His Lys Ala Pro Pro Glu Val Ser Leu Pro Leu
 65                  70                  75                  80

Met Ser Phe Arg Ser Asp Ala Trp Phe Cys Arg Trp Phe Glu Leu Glu
                85                  90                  95

Trp Leu Pro Gly Ala Ala Leu His Phe Pro Cys Tyr Gln Trp Leu Glu
               100                 105                 110

Gly Ala Gly Glu Leu Val Leu Arg Glu Gly Ala Ala Lys Val Ser Trp
           115                 120                 125

Gln Asp His His Pro Thr Leu Gln Asp Gln Arg Gln Lys Glu Leu Glu
       130                 135                 140

Ser Arg Gln Lys Met Tyr Ser Trp Lys Thr Tyr Ile Glu Gly Trp Pro
145                 150                 155                 160

Arg Cys Leu Asp His Glu Thr Val Lys Asp Leu Asp Leu Asn Ile Lys
                165                 170                 175

Tyr Ser Ala Met Lys Asn Ala Lys Leu Phe Phe Lys Ala His Ser Ala
               180                 185                 190

Tyr Thr Glu Leu Lys Val Lys Gly Leu Leu Asp Arg Thr Gly Leu Trp
           195                 200                 205
```

```
Arg Ser Leu Arg Glu Met Arg Arg Leu Phe Asn Phe Arg Lys Thr Pro
    210                 215                 220
Ala Ala Glu Tyr Val Phe Ala His Trp Gln Glu Asp Ala Phe Ala
225                 230                 235                 240
Ser Gln Phe Leu Asn Gly Ile Asn Pro Val Leu Ile Arg Arg Cys His
                245                 250                 255
Ser Leu Pro Asn Asn Phe Pro Val Thr Asp Glu Met Val Ala Pro Val
            260                 265                 270
Leu Gly Pro Gly Thr Ser Leu Gln Ala Glu Leu Glu Lys Gly Ser Leu
        275                 280                 285
Phe Leu Val Asp His Gly Ile Leu Ser Gly Val His Thr Asn Ile Leu
290                 295                 300
Asn Gly Lys Pro Gln Phe Ser Ala Ala Pro Met Thr Leu Leu His Gln
305                 310                 315                 320
Ser Ser Gly Ser Gly Pro Leu Leu Pro Ile Ala Ile Gln Leu Lys Gln
                325                 330                 335
Thr Pro Gly Pro Asp Asn Pro Ile Phe Leu Pro Ser Asp Asp Thr Trp
            340                 345                 350
Asp Trp Leu Leu Ala Lys Thr Trp Val Arg Asn Ser Glu Phe Tyr Ile
        355                 360                 365
His Glu Ala Val Thr His Leu Leu His Ala His Leu Ile Pro Glu Val
370                 375                 380
Phe Ala Leu Ala Thr Leu Arg Gln Leu Pro Arg Cys His Pro Leu Phe
385                 390                 395                 400
Lys Leu Leu Ile Pro His Ile Arg Tyr Thr Leu His Ile Asn Thr Leu
                405                 410                 415
Ala Arg Glu Leu Leu Val Ala Pro Gly Lys Leu Ile Asp Lys Ser Thr
            420                 425                 430
Gly Leu Gly Thr Gly Gly Phe Ser Asp Leu Ile Lys Arg Asn Met Glu
        435                 440                 445
Gln Leu Asn Tyr Ser Val Leu Cys Leu Pro Glu Asp Ile Arg Ala Arg
450                 455                 460
Gly Val Glu Asp Ile Pro Gly Tyr Tyr Arg Asp Asp Gly Met Gln
465                 470                 475                 480
Ile Trp Gly Ala Ile Lys Ser Phe Val Ser Glu Ile Val Ser Ile Tyr
                485                 490                 495
Tyr Pro Ser Asp Thr Ser Val Gln Asp Gln Glu Leu Gln Ala Trp
            500                 505                 510
Val Arg Glu Ile Phe Ser Glu Gly Phe Leu Gly Arg Glu Ser Ser Gly
        515                 520                 525
Met Pro Ser Leu Leu Asp Thr Arg Glu Ala Leu Val Gln Tyr Ile Thr
530                 535                 540
Met Val Ile Phe Thr Cys Ser Ala Lys His Ala Ala Val Ser Ser Gly
545                 550                 555                 560
Gln Phe Asp Ser Cys Val Trp Met Pro Asn Leu Pro Pro Thr Met Gln
                565                 570                 575
Leu Pro Pro Pro Thr Ser Lys Gly Gln Ala Arg Pro Glu Ser Phe Ile
            580                 585                 590
Ala Thr Leu Pro Ala Val Asn Ser Ser Tyr His Ile Ile Ala Leu
        595                 600                 605
Trp Leu Leu Ser Ala Glu Pro Gly Asp Gln Arg Pro Leu Gly His Tyr
610                 615                 620
```

```
Pro Asp Glu His Phe Thr Glu Asp Ala Pro Arg Arg Ser Val Ala Ala
625                 630                 635                 640

Phe Gln Arg Lys Leu Ile Gln Ile Ser Lys Gly Ile Arg Glu Arg Asn
            645                 650                 655

Arg Gly Leu Ala Leu Pro Tyr Thr Tyr Leu Asp Pro Pro Leu Ile Glu
        660                 665                 670

Asn Ser Val Ser Ile
        675

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 5:

Trp Leu Leu Ala Lys
1               5

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: N=i=inosine
        (B) LOCATION: 12, 15, 18
        (C) IDENTIFICATION METHOD:
        (D) OTHER INFORMATION:

(xi) SEQUENCE DESCRIPTION: SEQ ID NO: 6:

GACGTCTGGY TNYTNGCNAA  A                                      21

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: N=i=inosine
        (B) LOCATION: 12, 15, 18
        (C) IDENTIFICATION METHOD:
        (D) OTHER INFORMATION:

(xi) SEQUENCE DESCRIPTION: SEQ ID NO: 7:

GACGTCTGGY TNYTNGCNAA G                                       21

(2) INFORMATION FOR SEQ ID NO: 8:

(i) SEQUENCE CHARACTERISTICS:
        (A) LENGTH: 5 amino acids
        (B) TYPE: amino acid
        (C) STRANDEDNESS: single
        (D) TOPOLOGY: unknown (xi) SEQUENCE DESCRIPTION: SEQ ID NO: 8:

Gly Gln Leu Asp Trp
1               5
```

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 9:

```
CCAAGTGTAC CARTCNAGYT GNCC                                           24
```

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 10:

```
CCAAGTGTAC CARTCRTAYT GNCC                                           24
```

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ix) FEATURE:
        (A) NAME/KEY: N=i=inosine
        (B) LOCATION: 24, 25
        (C) IDENTIFICATION METHOD:
        (D) OTHER INFORMATION:

(xi) SEQUENCE DESCRIPTION: SEQ ID NO: 11:

```
TAGTCGACTG GCTTYTGGCC AAANNCTGGG TSCG                                34
```

(2) INFORMATION FOR SEQ ID NO: 12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 12:

```
GCGGATCCCT CCACCAGGNY TGSAGYTC                                       28
```

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 13:

```
GGTATCTACT ACCCAAGTGA TGAG                                           24
```

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (xi) SEQUENCE DESCRIPTION: SEQ ID NO: 14:

TACCCAAGTG ATGAGTCTGT C                                    21

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 15:

GAAGACCTCA GGCAGCAGAT GTG                                  23

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 16:

TCATGGAAGG AGAACTCGGC AT                                   22

(2) INFORMATION FOR SEQ ID NO: 17:

(i) SEQUENCE CHARACTERISTICS:
        (A) LENGTH: 31
        (B) TYPE: nucleic acid
        (C) STRANDEDNESS: single
        (D) TOPOLOGY: linear (xi) SEQUENCE DESCRIPTION: SEQ ID NO: 17:

ACGGATCCAG CATGGCCGAG TTCAGGGTCA G                          31

(2) INFORMATION FOR SEQ ID NO: 18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 18:

CGGAATTCAT GTCATCTGGG CCTGTGTTCC                            30

(2) INFORMATION FOR SEQ ID NO: 19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 19:

TGCCTCTCGC CATCCAGCT                                       19

(2) INFORMATION FOR SEQ ID NO: 20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 20:

TGTTCCCCTG GGATTTAGAT GGA                                         23

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 21:

GGTATCTACT ACCCAAGTGA TGAG                                        24

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 22:

TGGGATGTCA TCTGGGCCTG T                                           21

(2) INFORMATION FOR SEQ ID NO: 23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 23:

AACTCACCCC CACCACCATA CACA                                        24

(2) INFORMATION FOR SEQ ID NO: 24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 24:

TTCCCGCCTC CATCTCCCAA AGT                                         23

(2) INFORMATION FOR SEQ ID NO: 25:

(i) SEQUENCE CHARACTERISTICS:
        (A) LENGTH: 662 amino acids
        (B) TYPE: amino acid
        (C) STRANDEDNESS: single
        (D) TOPOLOGY: unknown (xi) SEQUENCE DESCRIPTION: SEQ ID NO: 25:

Met Gly Leu Tyr Arg Ile Arg Val Ser Thr Gly Ala Ser Leu Tyr Ala
 1               5                  10                  15

Gly Ser Asn Asn Gln Val Gln Leu Trp Leu Val Gly Gln His Gly Glu
            20                  25                  30

Ala Ala Leu Gly Lys Arg Leu Trp Pro Ala Arg Gly Lys Glu Thr Glu
        35                  40                  45

Leu Lys Val Glu Val Pro Glu Tyr Leu Gly Pro Leu Leu Phe Val Lys
    50                  55                  60

Leu Arg Lys Arg His Leu Leu Lys Asp Asp Ala Trp Phe Cys Asn Trp

-continued

```
                65                  70                  75                  80
            Ile Ser Val Gln Gly Pro Gly Ala Gly Asp Glu Val Arg Phe Pro Cys
                            85                  90                  95
            Tyr Arg Trp Val Glu Gly Asn Gly Val Leu Ser Leu Pro Glu Gly Thr
                           100                 105                 110
            Gly Arg Thr Val Gly Glu Asp Pro Gln Gly Leu Phe Gln Lys His Arg
                           115                 120                 125
            Glu Glu Glu Leu Glu Glu Arg Arg Lys Leu Tyr Arg Trp Gly Asn Trp
                           130                 135                 140
            Lys Asp Gly Leu Ile Leu Asn Met Ala Gly Ala Lys Leu Tyr Asp Leu
            145                 150                 155                 160
            Pro Val Asp Glu Arg Phe Leu Glu Asp Lys Arg Val Asp Phe Glu Val
                           165                 170                 175
            Ser Leu Ala Lys Gly Leu Ala Asp Leu Ala Ile Lys Asp Ser Leu Asn
                           180                 185                 190
            Val Leu Thr Cys Trp Lys Asp Leu Asp Asp Phe Asn Arg Ile Phe Trp
                           195                 200                 205
            Cys Gly Gln Ser Lys Leu Ala Glu Arg Val Arg Asp Ser Trp Lys Glu
                           210                 215                 220
            Asp Ala Leu Phe Gly Tyr Gln Phe Leu Asn Gly Ala Asn Pro Val Val
            225                 230                 235                 240
            Leu Arg Arg Ser Ala His Leu Pro Ala Arg Leu Val Phe Pro Pro Gly
                           245                 250                 255
            Met Glu Glu Leu Gln Ala Gln Leu Glu Lys Glu Leu Glu Gly Gly Thr
                           260                 265                 270
            Leu Phe Glu Ala Asp Phe Ser Leu Leu Asp Gly Ile Lys Ala Asn Val
                           275                 280                 285
            Ile Leu Cys Ser Gln Gln His Leu Ala Ala Pro Leu Val Met Leu Lys
                           290                 295                 300
            Leu Gln Pro Asp Gly Lys Leu Leu Pro Met Val Ile Gln Leu Gln Leu
            305                 310                 315                 320
            Pro Arg Thr Gly Ser Pro Pro Pro Leu Phe Leu Pro Thr Asp Pro
                           325                 330                 335
            Pro Met Ala Trp Leu Leu Ala Lys Cys Trp Val Arg Ser Ser Asp Phe
                           340                 345                 350
            Gln Leu His Glu Leu Gln Ser His Leu Leu Arg Gly His Leu Met Ala
                           355                 360                 365
            Glu Val Ile Val Ala Thr Met Arg Cys Leu Pro Ser Ile His Pro
            370                 375                 380
            Ile Phe Lys Leu Ile Ile Pro His Leu Arg Tyr Thr Leu Glu Ile Asn
            385                 390                 395                 400
            Val Arg Ala Arg Thr Gly Leu Val Ser Asp Met Gly Ile Phe Asp Gln
                           405                 410                 415
            Ile Met Ser Thr Gly Gly Gly His Val Gln Leu Leu Lys Gln Ala
                           420                 425                 430
            Gly Ala Phe Leu Thr Tyr Ser Ser Phe Cys Pro Pro Asp Leu Ala
                           435                 440                 445
            Asp Arg Gly Leu Leu Gly Val Lys Ser Ser Phe Tyr Ala Gln Asp Ala
            450                 455                 460
            Leu Arg Leu Trp Glu Ile Ile Tyr Arg Tyr Val Glu Gly Ile Val Ser
            465                 470                 475                 480
            Leu His Tyr Lys Thr Asp Val Ala Val Lys Asp Asp Pro Glu Leu Gln
                           485                 490                 495
```

```
Thr Trp Cys Arg Glu Ile Thr Glu Ile Gly Leu Gln Gly Ala Gln Asp
            500                 505                 510

Arg Gly Phe Pro Val Ser Leu Gln Ala Arg Asp Gln Val Cys His Phe
            515                 520                 525

Val Thr Met Cys Ile Phe Thr Cys Thr Gly Gln His Ala Ser Val His
            530                 535                 540

Leu Gly Gln Leu Asp Trp Tyr Ser Trp Val Pro Asn Ala Pro Cys Thr
545                 550                 555                 560

Met Arg Leu Pro Pro Thr Thr Lys Asp Ala Thr Leu Glu Thr Val
                565                 570                 575

Met Ala Thr Leu Pro Asn Phe His Gln Ala Ser Leu Gln Met Ser Ile
            580                 585                 590

Thr Trp Gln Leu Gly Arg Arg Gln Pro Val Met Val Ala Val Gly Gln
            595                 600                 605

His Glu Glu Glu Tyr Phe Ser Gly Pro Glu Pro Lys Ala Val Leu Lys
            610                 615                 620

Lys Phe Arg Glu Glu Leu Ala Ala Leu Asp Lys Glu Ile Glu Ile Arg
625                 630                 635                 640

Asn Ala Lys Leu Asp Met Pro Tyr Glu Tyr Leu Arg Pro Ser Val Val
                645                 650                 655

Glu Asn Ser Val Ala Ile
            660

(2) INFORMATION FOR SEQ ID NO: 26:

(i) SEQUENCE CHARACTERISTICS:
        (A) LENGTH: 7 amino acids
        (B) TYPE: amino acid
        (C) STRANDEDNESS: single
        (D) TOPOLOGY: unknown (xi) SEQUENCE DESCRIPTION: SEQ ID NO: 26:

Glu Leu Gln Xaa Trp Trp Tyr
1               5

(2) INFORMATION FOR SEQ ID NO: 27:

(i) SEQUENCE CHARACTERISTICS:
        (A) LENGTH: 7 amino acids
        (B) TYPE: amino acid
        (C) STRANDEDNESS: single
        (D) TOPOLOGY: unknown (xi) SEQUENCE DESCRIPTION: SEQ ID NO: 27:

Asp Val Trp Leu Leu Ala Lys
1               5

(2) INFORMATION FOR SEQ ID NO: 28:

(i) SEQUENCE CHARACTERISTICS:
        (A) LENGTH: 5 amino acids
        (B) TYPE: amino acid
        (C) STRANDEDNESS: single
        (D) TOPOLOGY: unknown (xi) SEQUENCE DESCRIPTION: SEQ ID NO: 28:

Gly Gln Phe Asp Ser
1               5

(2) INFORMATION FOR SEQ ID NO: 29:
```

```
    (i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 29:

CCAAGCGCAS SARTCRAAYT GNCC                                              24

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 30:

GAGCTTTGTC TCTGAAATAG TCAG                                              24

(2) INFORMATION FOR SEQ ID NO: 31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 31:

GTGAGGAATC AATAGCTTGA AGAG                                              24

(2) INFORMATION FOR SEQ ID NO: 32:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 32:

GATGTGTGAC AGCCTCATGG ATG                                               23

(2) INFORMATION FOR SEQ ID NO: 33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 33:

CAAGCTTAGG AGGATGGCGA AATGCAGG                                          28

(2) INFORMATION FOR SEQ ID NO: 34:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 34:

GGAATTCATG TTAGATGGAG ACACTGTT                                          28

(2) INFORMATION FOR SEQ ID NO: 35:

(i) SEQUENCE CHARACTERISTICS:
```

```
        (A) LENGTH: 5 amino acids
        (B) TYPE: amino acid
        (C) STRANDEDNESS: single
        (D) TOPOLOGY: unknown (xi) SEQUENCE DESCRIPTION: SEQ ID NO: 35:

Gly Gln Tyr Asp Trp
1               5

(2) INFORMATION FOR SEQ ID NO: 36:

(i) SEQUENCE CHARACTERISTICS:
        (A) LENGTH: 13 amino acids
        (B) TYPE: amino acid
        (C) STRANDEDNESS: single
        (D) TOPOLOGY: unknown (xi) SEQUENCE DESCRIPTION: SEQ ID NO: 36:

Xaa Val Asp Trp Leu Leu Ala Ala Lys Xaa Trp Val Arg
1               5                   10
```

It will be understood that various details of the invention may be changed without departing from the scope of the invention. Furthermore, the foregoing description is for the purpose of illustration only, and not for the purpose of limitation—the invention being defined by the claims.

What is claimed is:

1. An isolated and purified biologically active 15-Lox-2 polypeptide capable of converting arachidonic acid exclusively to 15S-hydroperoxyeicosatetraenoic acid, said 15-Lox-2 polypeptide containing an iron ligand comprising a serine, wherein the 15-Lox-2 polypeptide comprises an amino acid sequence at least 80% identical to the amino acid sequence of SEQ ID NO:2.

2. A polypeptide of claim 1, wherein said polypeptide has an in vivo molecular weight of about 76 KD when measured by SDS-PAGE.

3. A polypeptide of claim 1 further comprising an amino acid sequence W-L-L-A-K (SEQ ID NO: 5) and an amino acid sequence G-Q-Y-D-W (SEQ ID NO: 35) wherein, the amino acid sequence W-L-L-A-K (SEQ ID NO: 5) is positioned upstream from the amino acid sequence G-Q-Y-D-W (SEQ ID NO: 35).

4. An isolated and purified biologically active 15-Lox-2 polypeptide, capable of converting arachidonic acid exclusively to 15S-hydroperoxyeicosatetraenoic acid, the 15-Lox-2 polypeptide containing an iron ligand comprising a serine, wherein the 15-Lox-2 polypeptide comprises the amino acid sequence of SEQ ID NO:2.

5. A polypeptide according to claim 4, modified to be in detectably labeled form.

6. A diagnostic assay kit for detecting the presence, in a biological sample, of an antibody immunoreactive with a 15-Lox-2 polypeptide, the kit comprising a first container containing a 15-Lox-2 polypeptide of claim 4 that immunoreacts with the antibody, with the polypeptide present in an amount sufficient to perform at least one assay for the antibody.

* * * * *